(12) United States Patent
Basude

(10) Patent No.: US 11,701,493 B2
(45) Date of Patent: Jul. 18, 2023

(54) TISSUE GRASPING DEVICES AND RELATED METHODS

(71) Applicant: Raghuveer Basude, Fremont, CA (US)

(72) Inventor: Raghuveer Basude, Fremont, CA (US)

(*) Notice: Subject to any disclaimer, the term of this patent is extended or adjusted under 35 U.S.C. 154(b) by 443 days.

(21) Appl. No.: 16/844,338

(22) Filed: Apr. 9, 2020

(65) Prior Publication Data

US 2020/0230362 A1    Jul. 23, 2020

Related U.S. Application Data

(63) Continuation of application No. PCT/US2018/055259, filed on Oct. 10, 2018.

(60) Provisional application No. 62/570,270, filed on Oct. 10, 2017.

(51) Int. Cl.
*A61M 25/02* (2006.01)
*A61F 2/24* (2006.01)
*A61M 25/01* (2006.01)
*A61B 17/00* (2006.01)
*A61M 25/06* (2006.01)

(52) U.S. Cl.
CPC .......... *A61M 25/02* (2013.01); *A61F 2/2427* (2013.01); *A61M 25/0113* (2013.01); *A61B 2017/00292* (2013.01); *A61M 25/0116* (2013.01); *A61M 2025/024* (2013.01); *A61M 2025/028* (2013.01); *A61M 2025/0681* (2013.01)

(58) Field of Classification Search
CPC ......... A61B 90/50; A61B 2017/00292; A61M 2025/028; A61M 2025/024; A61M 25/02; A61M 25/0116; A61M 25/0113; A61M 2025/0681
See application file for complete search history.

(56) References Cited

U.S. PATENT DOCUMENTS

| | | |
|---|---|---|
| 4,224,937 A | 9/1980 | Gordon |
| 7,226,467 B2 | 6/2007 | Lucatero et al. |
| 8,057,493 B2 | 11/2011 | Goldfarb et al. |

(Continued)

FOREIGN PATENT DOCUMENTS

| | | |
|---|---|---|
| CN | 101594816 A | 12/2009 |
| CN | 105658164 A | 6/2016 |

(Continued)

OTHER PUBLICATIONS

International Search Report and Written Opinion for PCT/US2018/055259 dated Dec. 26, 2018.
EP18866289.4 Extended Search Report dated May 17, 2021.

*Primary Examiner* — Deanna K Hall
(74) *Attorney, Agent, or Firm* — Wilson Sonsini Goodrich & Rosati

(57) ABSTRACT

The present disclosure relates generally to systems, devices, and methods for supporting, stabilizing, and/or positioning a medical device, such as a transcatheter medical device. The stabilizer allows for control of degrees of freedom from no movement to free movement to selective movements, to substantially translation only movement and/or to substantially rotational only movement of the medical device. The patent describes pure mechanical embodiment as well as smart embodiments that can synergistically sense, actuate and/or transmit data between the stabilizer, medical device and control or display system to operate and/or deploy the device/therapy.

17 Claims, 19 Drawing Sheets

(56) References Cited

U.S. PATENT DOCUMENTS

| | | |
|---|---|---|
| 8,740,920 B2 | 6/2014 | Goldfarb et al. |
| 2002/0143235 A1 | 10/2002 | Pagliuca |
| 2004/0089777 A1 | 5/2004 | Schilt et al. |
| 2007/0055109 A1 | 3/2007 | Bass et al. |
| 2007/0158513 A1 | 7/2007 | Levahn et al. |
| 2010/0160825 A1 | 6/2010 | Parihar et al. |
| 2011/0306934 A1 | 12/2011 | Haider et al. |
| 2012/0118088 A1 * | 5/2012 | Smith ............... A61B 1/00154 |
| | | 384/15 |
| 2012/0172850 A1 | 7/2012 | Kappel et al. |
| 2014/0324024 A1 | 10/2014 | Tejani |
| 2016/0030036 A1 | 2/2016 | Belman et al. |
| 2017/0100201 A1 | 4/2017 | Ho et al. |
| 2019/0030285 A1 | 1/2019 | Prabhu et al. |
| 2020/0229806 A1 | 7/2020 | Goldfarb et al. |

FOREIGN PATENT DOCUMENTS

| | | | | |
|---|---|---|---|---|
| WO | WO-2017062637 A1 * | 4/2017 | ............. | A61B 90/11 |
| WO | WO-2017062640 A1 | 4/2017 | | |
| WO | WO-2019075095 A1 | 4/2019 | | |

* cited by examiner

TISSUE GRASPING DEVICES AND RELATED METHODS

CROSS-REFERENCE TO RELATED APPLICATIONS

This application is a continuation of PCT Application No. PCT/US18/55259, filed Oct. 10, 2018, which claims the benefit of Provisional Application No. 62/570,270, filed Oct. 10, 2017, the entire content of which is incorporated herein in its entirety.

BACKGROUND OF THE INVENTION

1. Field of the Invention

The present disclosure relates generally to systems, devices, and methods for supporting, stabilizing, and/or positioning a medical device, such as a transcatheter medical device. In particular, the present invention relates to methods, devices, and systems for the endovascular, percutaneous, or minimally invasive surgical treatment of bodily tissues, such as tissue approximation or valve repair. More particularly, the present invention relates to methods and devices for the repair of mitral and tricuspid heart valves, venous valves, and other tissue structure through minimally invasive and other procedures.

Various medical procedures require the controlled use of medical devices. Typically, during such a medical procedure, a portion of a medical device must be positioned near a patient's body or near a surgical site during the medical procedure. Often, during such procedures, the medical device must be manipulated and repositioned, and in many instances one portion of the medical device must be moved relative to another portion of the medical device. On the other hand, inadvertent movement or unintended positioning of the medical device during a delicate medical procedure is undesirable and can be dangerous to the patient, particularly when there are portions of the medical device, such as a catheter or implant, that have been positioned within the body.

A medical device can be positioned on a stabilizer and fixed in place relative to patient and/or surgical table, to reduce the risk of inadvertent movement of the medical device. However, the stabilizer must also allow for controlled repositioning of the medical device as required during the procedure (for example, some manipulations may require that the stabilizer allows for the device to be rotated while restricting translational displacement of the device). Current stabilizers (for example and not limited to this example—stabilizer of MitraClip fixation device as per U.S. Pat. No. 8,740,920, sold by Abbott Vascular, Santa Clara, Calif., USA), do not reliably accomplish this important task, as the device gets unconstrained in both rotation and translation. Thereby, reintroducing the very risks the stabilizer was intended to limit. New patent applications (U.S. Patent Publication No. 2017/0100201; PCT/US2016/055777; WO 2017/062637 A1) attempt to address some of the limitations of the current stabilizer, however, is much more complicated, less intuitive and with reduced or no tactile feedback. For example, it allows for controlled rotation of guide while fixing the translation motion. If translation motion is required, the entire stabilizer platform needs to be moved using a screw lever, which in addition to being complicated and cumbersome, loses the desired tactile feedback.

Similarly, most of the competitor stabilizers are complicated, bulky to handle and difficult to store (hospitals typically have limited storage space).

For at least these aforementioned reasons, there is an ongoing need for an improved stabilizer. Specifically, a stabilizer must possess the following characteristics a) easy, simple and intuitive to use, b) easy to clean, sterilize and store, c) fulfill required biocompatibility requirements, d) durable and safe to operate, e) quick engagement and disengagement of the catheter from the stabilizer, f) allows for controlled translation and rotational motion of the catheter, g) allows for controlled rotation while restricting translation, h) allows for quick fixation of the catheter in a desired position and i) secures or supports the catheter and/or delivery catheter system during use.

2. Description of the Background Art

Catheter holding devices and similar apparatus are described in U.S. Pat. Nos. 8,740,920; 8,057,493; 7,226,467; US Pat. Publ. No. 2017/0100201; PCT Publication No. WO2017/062637; and PCT Publication No. WO2017/062640.

SUMMARY OF THE INVENTION

In a first aspect, the present invention provides a catheter deployment system which includes a first catheter having a body with a distal end and a proximal hub. Gripping features are formed on the catheter body distal of the proximal hub, typically being immediately proximal of the distal side of the hub. A free-standing support structure has at least one support post, and a clamp structure is disposed on the support structure, typically at a vertically upper end thereof. The clamp structure has an opened position, a closed position, and a plurality of intermediate positions between the open position and the closed position. The gripping features are configured to interact with the clamp structure to allow a user to selectively lock, partially lock, and unlock the first catheter relative to the support structure. In particular, the gripping features may be configured so that the catheter body may be freely inserted into and removed from the clamp structure when the clamp structure is in its opened configuration. When the clamp structure is in a first intermediate position, the gripping features and the clamp structure will engage or otherwise interlock to allow the catheter body to be both rotated and axially translated relative to the clamp structure while the first catheter otherwise remains secured to the support structure by the clamp structure. When in a second intermediate position, the clamp structure will interface with the gripping features in such a way that rotation of the catheter body is permitted while axial translation in the catheter body is prevented. When fully closed, the clamp structure fully engages the gripping feature so that the catheter body can be neither rotated nor axially advanced, i.e., it will be immobilized relative to the free-standing support structure.

It will be appreciated that the availability of these options allows a user to conveniently manipulate the first catheter with a desired degree of freedom. That is, in the first intermediate position, the catheter body is secured to the support but remains free to rotate and axially translate to allow the user to position the distal end of the catheter body within the patient. Once an initially desired positioning is achieved, the clamp structure may be adjusted to its second intermediate position to allow rotation of the catheter body but preventing axial translation to permit fine positioning of the catheter. Once in a final desired location, the clamp structure may be fully closed to prevent both rotation and axially translation of the catheter body. The first catheter may, of course, be repositioned at any time by loosening the clamp structure to its first or second intermediate positions and repeating the positioning steps noted above.

Exemplary gripping features comprise circumferential ribs having valleys therebetween. Preferably, the ridges are fully circumferential so that adjacent ridges are not connected. In other embodiments, however, the ridges could be helical or screw-like, but such a helical structure will affect how the catheter is positioned as described below.

With such "rib-valley" gripping features, the clamp structure will typically include an engaging element positioned adjacent to the gripping features when the first catheter is in the clamp structure. The first catheter is removably placed in a slot, channel or other receiving portion of the clamp while the clamp structure and the clamp structure closed to a first intermediate position to secure the first catheter to the free-standing support structure. While the clamp structure remains in its first intermediate position, the engaging element remains sufficiently disengaged from the gripping features so that the first catheter can be both rotated and axially translated relative to the support structure. When a desired axial positioning of the first catheter has been achieved, the clamp structure can be further closed to the second intermediate position where the engaging element interacts with the gripping features in such a way that the engaging element prevents axial translation but allows rotation about the catheter axis, typically being advanced into the valley between adjacent ribs so that the catheter is free to rotate with the engaging element to travel circumferentially around the catheter within the valley. The ribs which define the valleys will prevent axial movement of the catheter.

In the illustrated embodiments, the ribs and valleys are a series of circular, circumferential structures so that the engaging element will be constrained in a single circumferential valley as the first catheter is rotated which will prevent any axial translation. In an alternative embodiment, the ribs and valleys could be arranged helically so that rotation of the first catheter will provide a controlled advancement or retraction of the catheter determined by the direction of rotation and the pitch of the helical pattern.

In specific embodiments, the first catheter may be a guiding catheter and the systems may further comprise a second catheter, such as an implant delivery catheter which is introduced through the guiding catheter. Typically, the second catheter is configured to be introduced through a lumen of the first catheter while the first (guiding) catheter is being held by on the support structure by the clamp structure. In order to support a handle or hub of the second catheter, the second catheter may have a rigid proximal shaft region that self-supports the handle or hub of the second catheter. Such a rigid proximal shaft region may be a metal or other rigid stress relief component extending distally from the hub or handle of the second catheter. Alternatively, a second support post may be provided on the support structure to support the hub or handle of the second catheter when the second catheter is extending proximally from a proximal end of the first catheter.

The clamp structure may have a variety of configurations. In one specific configuration a biasing member is configured to advance the gripping features toward the engaging element which is within a receiving slot or channel for first catheter. The biasing member may comprise, for example, a threaded shaft which can be screwed in and out of the clamp structure to tighten down on the gripping features when present in the clamp structure. In specific instances, the engaging element of the clamp structure may comprise a ribbed structure having surfaces that mate with the ribs of the gripping features on the catheter body. Thus, when the threaded shaft or other biasing member urges the ribs against the engaging element, the ribs of the engaging element will mesh the ribs of the gripping features so that the catheter body may be rotated (as the engagement ribs travel in the valleys of the gripping features) but not axially translated as the ribs of the gripping features and the ribs of the engaging element are in an interference fit.

In a second aspect, the present invention provides a method for supporting a first catheter during a procedure, typically an intravascular procedure where the first catheter is introduced into a femoral artery or other blood vessel. The method comprises providing a first catheter having a body with a distal end, a proximal hub and gripping features formed on the catheter body distal of the proximal hub. A support structure including at least one support post is also provided. The support structure includes a clamp structure having an open position, a closed position and a plurality of intermediate positions between the open and closed positions. The first catheter is placed on the support structure so that the gripping features are located within the clamp structure while the clamp structure is in the open position. Typically, the first catheter will be placed in a receiving slot or other receptacle of the clamp structure. The clamp structure is then closed to a first intermediate position over the gripping features, where the catheter body is free to rotate and/or axial translate about its central axis so long as this clamp structure remains in the first intermediate position. After axial positioning is achieved, the clamp structure will be closed further to a second intermediate position over the gripping features. While the clamp structure is in the second intermediate position, the first catheter may be rotated about its axis but will be prevented from axial translation by a mechanical interaction of the gripping features and the clamp structure as described previously. The methods of the present invention may further comprise fully closing the clamp structure to allow neither rotation nor axial translation of the first catheter.

As in the systems of the present invention described previously, preferred gripping features comprise circumferential ribs and valleys, and closing the clamp structure to its second intermediate position will advance an engaging element into the valley between adjacent ribs such that the catheter is free to rotate as the engaging element travels in the valley circumferentially but is constrained from axial movement by the ribs.

The methods herein may further comprise introducing a second catheter through a lumen of the first catheter is held on the support structure by the clamp structure. The methods typically further comprise supporting a hub or handle on the second catheter in tandem with the hub or handle on the first catheter, where the hub on the second catheter may be self-supporting, typically through a rigid proximal shaft region on the second catheter, or may be separately supported by a second support post on the support structure, and/or may be supported on a second stand-alone or interconnected support structure.

In a third aspect, the present invention provides a catheter suitable for use with the support structures and methods described previously. In particular, catheters according to the present invention comprise a catheter body with a distal end and a proximal hub. Gripping features are formed or otherwise provided on the catheter body distal of the proximal hub. For example, the gripping features may be part of a stress release structure at the proximal end of the catheter body and immediately distal to the proximal hub. The gripping features will be configured to be inserted into and removed from a clamp structure when the clamp structure is in an open configuration. The gripping features are further configured so that the catheter body may be rotated and axially translated within the clamp structure after the clamp structure has been partially closed to a first intermediate position. After the clamp structure is further closed to a second intermediate position, the gripping features are configured such that the catheter may be freely rotated but not axially translated. Additionally, when fully closed, the clamp structure will prevent both rotation and axial translation of the gripping feature and of the entire catheter. The specific structural details of the catheter of the present invention have been described previously in connection with the systems and methods of the present invention.

In a fourth aspect, the present invention provides a method for supporting a first and second catheter during a procedure, wherein, the first and second catheter have features to control motion relative to each other, typically in an intravascular procedure where the first catheter is introduced into a femoral artery or other blood vessel. The method comprises providing a first catheter having a body with a distal end, a proximal hub and gripping features formed on the catheter body distal of the proximal hub. A support structure including at least one support post is also provided. The support structure includes a clamp structure. Typically, the second catheter is configured to be introduced through a lumen of the first catheter while the first (guiding) catheter is being held by on the support structure by the clamp structure. In order to support a handle or hub of the second catheter relative to the first catheter, the second catheter may have a rigid proximal shaft region that self-supports the handle or hub of the second catheter. Such a rigid proximal shaft region may be a metal or other rigid stress relief component extending distally from the hub or handle of the second catheter. Additionally, the proximal end of the first catheter may have receiving clamp structure similar to the support structure and the metal or other rigid stress relief component extending distally from the hub or handle of the second catheter may have gripping features such as ribs or threads. Similar to the support structure clamp, the receiving structure of the first catheter can be configured to have an open position, a closed position and a plurality of intermediate positions between the open and closed positions. The second catheter is inserted in the first catheter so that the gripping features are located within the clamp structure of the first catheter while the clamp structure is in the open position. The clamp structure is then closed to a first intermediate position over the gripping features, where the second catheter body is free to rotate and/or axial translate about its central axis so long as this clamp structure remains in the first intermediate position. After axial positioning is achieved, the clamp structure will be closed further to a second intermediate position over the gripping features. While the clamp structure is in the second intermediate position, the second catheter may be rotated about its axis but will be prevented from axial translation by a mechanical interaction of the gripping features and the clamp structure as described previously. The methods of the present invention may further comprise fully closing the clamp structure to allow neither rotation nor axial translation of the second catheter, relative to the first catheter.

Other features of the present invention disclosed herein include a stable non-slip surface may be height or incline adjustable and/or articulated. The stable non-slip surface may be placed on the operating room table or attached or mounted on the side rails of the operating room (OR) table or an operating room floor stand/pole.

The present invention may provide a stabilizer comprising reusable and disposable components. Optionally, the stabilizer may be entirely made of single use sterile and disposable components. For example, it will be evident for those in the medical device field that the device interfacing stabilizer maybe completely made of single use sterile disposable component that is securely mounted on to a tray or feature that is in turn mounted on a standard side rail of an OR table.

The stabilizer may comprise of sensors and actuators for analog or digital display and/or remote control/feedback/assessment of position, rotation, translation, removal or attachment of the catheter/handle system.

The stabilizer and/or its components can be made of metals, alloys, ceramic, polymers, glass or any suitable ingredient of organic and/or inorganic in origin, and/or their combinations. For example, shape memory or superelastic polymers or alloys such as nitinol.

The stabilizer and other components that interface with the device or user may be coated or covered to improve aseptic or antiseptic or other present or future OR requirements.

Other objects and advantages of the present invention will become apparent from the detailed description to follow, together with the accompanying drawings and clauses.

As evident to those skilled in the art, variations of embodiments may be formed by combining or substituting various aspects or features or subcomponents and/or parts of various exemplary embodiments described above. For example, two or more stabilizers may be used independently or as a unit to control one or more catheters to perform the procedure (and/or supporting activities that are routinely performed during surgery, catheter based intervention, minimally invasive surgery, endoscopic and/or robotic procedures) such as and not limited to pressure sensing, contrast injection, ice catheter manipulation etc.

Any one of skill in the art would appreciate the various examples and embodiments and aspects described and claimed herein can be combined in part or in whole throughout this application.

The following numbered clauses describe examples, aspects, embodiments and potential claims of the inventions described herein:

1. A stabilizer comprising: a platform; a translation actuator coupled to the platform; and a rotation actuator coupled to the platform; and an angle actuator coupled to the platform 2. Stabilizer system of clause 1, wherein, all of the actuator systems are separate performing independent functions 3. Stabilizer system of clause 1, wherein, all or some of the actuator systems perform two or more actuation functions 4. Stabilizer system of clause 1, wherein, actuated motion may be in smooth increments or interrupted and set increments or their combination.

5. The stabilizer system of clause 1, wherein the translation actuator includes a leadscrew and the receiving member includes a nut configured to selectively engage or disengage with the leadscrew.

6. The stabilizer system of clause 1, wherein the rotational actuator includes a leadscrew and the receiving member includes a nut configured to selectively engage or disengage with the leadscrew.

7. The stabilizer system of clause 1, wherein the rotational or translational and/or incline angle can be selectively actuated within a set/limited range only.

8. The stabilizer system of clause 1, wherein the rotational and/or translational selectively actuated within a set/limited range and the incline angle is fixed in a preset configuration.

9. The stabilizer system of clause 1, wherein the medical device can be selectively and repeatedly engaged or disengaged/removed completely from the stabilizer during use.

10. The stabilizer system of clause 1, wherein the medical device can be selectively and repeatedly engaged or disengaged/removed completely from the stabilizer during use without requiring any disassembly of the medical device.

11. The stabilizer system of clause 1, wherein the medical device can be selectively and repeatedly engaged or disengaged/removed completely from the stabilizer during use and requiring limited or partial disassembly of the medical device.

12. A stabilizer system for supporting and actuating medical device comprising: a base; a translation actuator coupled to the base; and a rotation actuator coupled to the base; and an angle actuator coupled to the base; and a platform that securely and removably couples with the base 13. The stabilizer system of clause 12, wherein the platform can be securely and removably coupled with standard side rail of the OR table 14. The stabilizer system of clause 13, wherein the platform is coupled to the OR table via an articulate or bendable and/or lockable and repositionable coupling.

15. A passive stabilizer system for supporting and actuating medical device comprising: a base; a translation actuator coupled to the base; and a rotation actuator coupled to the base; and an angle actuator coupled to the base; and wherein, the position of the actuators can be sensed on a local display 16. A passive stabilizer system for supporting and actuating medical device comprising: a base; a translation actuator coupled to the base; and a rotation actuator coupled to the base; and an angle actuator coupled to the base; and wherein, the position of the actuators can be sensed on a remote display 17. An active and smart stabilizer system for supporting and actuating medical device comprising: a base; a translation actuator coupled to the base; and a rotation actuator coupled to the base; and an angle actuator coupled to the base; and wherein, the position of the actuators can be actuated, controlled and sensed 18. An active and smart stabilizer system for supporting and actuating medical device comprising: a base; a translation actuator coupled to the base; and a rotation actuator coupled to the base; and an angle actuator coupled to the base; and wherein, the position of the actuators can be actuated, controlled and sensed; and the stabilizer can power or sense and/or control the coupled medical device.

19. An active and smart stabilizer system for supporting and actuating medical device comprising: a base; a motorized translation actuator coupled to the base; and a motorized rotation actuator coupled to the base; and a motorized angle actuator coupled to the base; and wherein, the position of the actuators can be actuated, controlled and sensed wirelessly onto a control module; and the stabilizer can power or sense and/or control the coupled medical device.

20. An active and smart stabilizer system for supporting and actuating medical device comprising: a base; a motorized translation actuator coupled to the base; and a motorized rotation actuator coupled to the base; and a motorized angle actuator coupled to the base; and wherein, the position of the actuators can be actuated, controlled and sensed and displayed on to a control module.

21. An active and smart stabilizer system for supporting and actuating medical device comprising: a base; a motorized translation actuator coupled to the base; and a motorized rotation actuator coupled to the base; and a motorized angle actuator coupled to the base; and wherein, the position of the actuators can be actuated, controlled and sensed and displayed on to a control module; and a smart interface between the stabilizer and medical device for a synergetic control with feedback between the stabilizer and medical device use/function.

22. An active and smart robotic stabilizer system for supporting and actuating robotic medical device comprising: a base; a motorized robotic arm coupled to the base; and a motorized translation actuator coupled to the base; and a motorized rotation actuator coupled to the base; and a motorized angle actuator coupled to the base; and wherein, the position of the actuators can be actuated, controlled and sensed and displayed on to a control module; and a robotic control and interface between the device, catheter, and the stabilizer; and a smart interface between the stabilizer and medical device for a synergetic control with user feedback between the stabilizer and medical device use/function.

23. Any stabilizer described in these clauses, wherein, the medical device handle can be angled between a)+180 degrees and −180 degrees from the horizontal, b)+90 degrees and −90 degrees from the horizontal, c)+45 degrees and −45 degrees from the horizontal, d)+20 degrees and −20 degrees from the horizontal, e)+10 degrees and −10 degrees from horizontal, e)+5 degrees and −5 degrees from horizontal 24. Any stabilizer described in these clauses, wherein, the medical device can be selectively manipulated or fixed along any or all degrees of freedom, for example and not limited to example, a) translated and/or fixed along x-axis, y-axis and z-axis, b) rotated and/or fixed along x-axis, y-axis and z-axis, angled between, c) including manipulation along other degrees of freedom such as time.

25. Any stabilizer described in these clauses, wherein, the medical device can be selectively manipulated or fixed along any or all degrees of freedom, for example and not limited to example, a) translated and/or fixed along x-axis, y-axis and z-axis, b) rotated and/or fixed along x-axis, y-axis and z-axis, angled between, c) including manipulation along other degrees of freedom such as time, wherein; the translation is can be between 0 mm to infinity (absolute), 0 mm and 10 m (absolute); 0 mm and 1 m (absolute); 0 mm and 0.5 m (absolute); 0 mm and 0.25 m (absolute); 0 mm and 100 mm (absolute); 0 mm and 10 mm (absolute); 0 mm and 5 mm (absolute); wherein; the rotation can be between 0 and 180 degrees (absolute); 0 and 90 degrees (absolute); 0 and 45 degrees (absolute); 0 and 30 degrees (absolute); 0 and 20 degrees (absolute); 0 and 10 degrees (absolute); 0 and 5 degrees (absolute); 0 and 3 degrees (absolute); wherein, the time can be between 0 hrs and infinity; 0 hrs and >30 days; 0 hrs and >1 days; 0 hrs and <1 day; 0 hrs and 12 hrs; 0 hrs and 6 hrs; 0 hrs and 3 hrs; 0 hrs and 2 hrs; 0 hrs and 2 hrs; 0 hrs and 1 hr; 0 minutes and 30 minutes; 0 minutes and 15 minutes; 0 minutes and 5 minutes; 0 minutes and <1 minutes; and/or any combination and/or variations of these manipulations 26. Any stabilizer described in these clauses, wherein, it actively or passively interacts with the delivery system or implant and/or medical device, in order to aid or assist the medical procedure.

27. Any smart, active and/or passive stabilizer described in this application, comprising of bi-directional communication or interaction between the stabilizer and the medical device; wherein, the system (stabilizer and the medical device) can autonomously perform the procedure.

28. Any smart, active and/or passive stabilizer described in this application, comprising of multi and/or bi-directional communication or interaction between the stabilizer and the medical device; wherein, the system (stabilizer and the medical device) can autonomously perform the procedure with cue from the human operator.

29. Any smart, active and/or passive stabilizer described in this application, comprising of communication, interaction, artificial intelligence, deep learning awareness between the stabilizer and the medical device; wherein, the system (stabilizer and the medical device) can autonomously perform partial or full procedure with cue from remote human and/or robotic operator.

30. As evident to those skilled in the art, variations of embodiments (and clauses) may be formed by combining or substituting various aspects or features or subcomponents and/or parts of various exemplary embodiments described above. For example, two or more stabilizers may be used independently or as a unit to control one or more catheters to perform the procedure (and/or supporting activities that are routinely performed during surgery, catheter-based intervention, minimally invasive surgery, endoscopic and/or robotic procedures) such as and not limited to pressure sensing, contrast injection, 3D position sensing, 3D location imaging, medical (for example optical) imaging, ice catheter manipulation/integration etc.

31. Any one of skill in the art would appreciate, most catheters and device handles comprise of pulling, pushing, rotating, and/or translating to operate the device delivery system. While in conventional catheters, cannulae, endoscope etc. these manipulations are achieved by hand, these motions can easily be reproduced using of motors, actuators, transducers, sensors, gears, levers and/or other common programmable, remote controlled and/or robotic methods. The stabilizer in this invention can be configured to interface with the medical device handle and/or the internal mechanisms of the handle-interface, to operate, control and delivery the device or the therapy.

32. Any one of skill in the art would appreciate, the various examples and embodiments and aspects described and claimed in the clauses herein can be combined in part or in whole throughout this application to perform a structural heart procedures (example mitral valve repair/replacement, tricuspid valve repair/replacement, aortic valve repair/replacement), interventional procedures such as placement of stents, electrodes, implants, ablations, suturing, chemical and radiologic therapy, and other minimally invasive and endoscopic procedures.

33. Any one of skill in the art would appreciate the various examples and embodiments and aspects described and claimed in the clauses herein can be combined in part or in whole throughout this application. For example, the relative or absolute translation, rotation, engaging and disengaging actuation described in the above clauses can be performed between a) support structure (stabilizer) and guide catheter, b) guide catheter and delivery catheter and/or c) stabilizer, guide catheter and/or delivery catheter.

34. A catheter system of claims 1 to 22 and above clauses, wherein, a hemostasis valve is incorporated into the guide handle 34.

35. A catheter system of claims 1 to 22 and above clauses, wherein, a hemostasis valve is incorporated into the guide catheter handle 34 and delivery catheter handle 44.

36. A catheter system of claims 1 to 22 and above clauses, wherein, a hemostasis valve is incorporated into the guide handle 34, and is configured to provide hemostasis while allowing insertion and removal of dilator, delivery catheter and/or other interventional devices/accessories.

37. A catheter system of claims 1 to 22 and above clauses comprising, a delivery catheter having a body with a distal end and a proximal hub; and gripping features on the delivery catheter body distal of the proximal hub; a guide catheter having a body with a lumen; and clamp features in the guide catheter body lumen; wherein (a) the gripping features of the delivery catheter body are configured to be inserted into and removed from a clamp structure when the clamp structure is in its opened configuration, (b) the gripping features of the delivery catheter body may be rotated and axially translated within the clamp structure when the clamp structure is in a first intermediate position, and (c) the gripping features of the delivery catheter body may be rotated but not axially translated within the clamp structure when the clamp structure is in a second intermediate position.

38. A catheter system of clause 37, wherein, the gripping feature comprises of ribs, slots, directional and/or non-directional frictional features, active and/or passive actuators commonly known to those skilled in the art.

DETAILED DESCRIPTION OF THE INVENTION

Critical interventional procedures such as mitral valve repair or replacement require that the catheters be positioned in certain orientation. Further, the procedural requires quick and controlled manipulations in certain directions while restricting movement in other directions. For example, during repair of the mitral valve, it may be necessary to rotate the steerable guide while restricting large or sudden translational movements. Failure to prevent unintended motion can lead to significant risks to the patients and/or to the success of the procedure. Hence, stabilizers are used in such critical interventional or minimally invasive procedure.

The present disclosure relates to devices, systems, and methods for supporting, stabilizing, and positioning a medical device. Typically, such medical devices are catheter based. Certain embodiments can advantageously allow adjustment and/or positioning of a medical device while maintaining stable support of the medical device upon the stabilizer.

Figure 1:
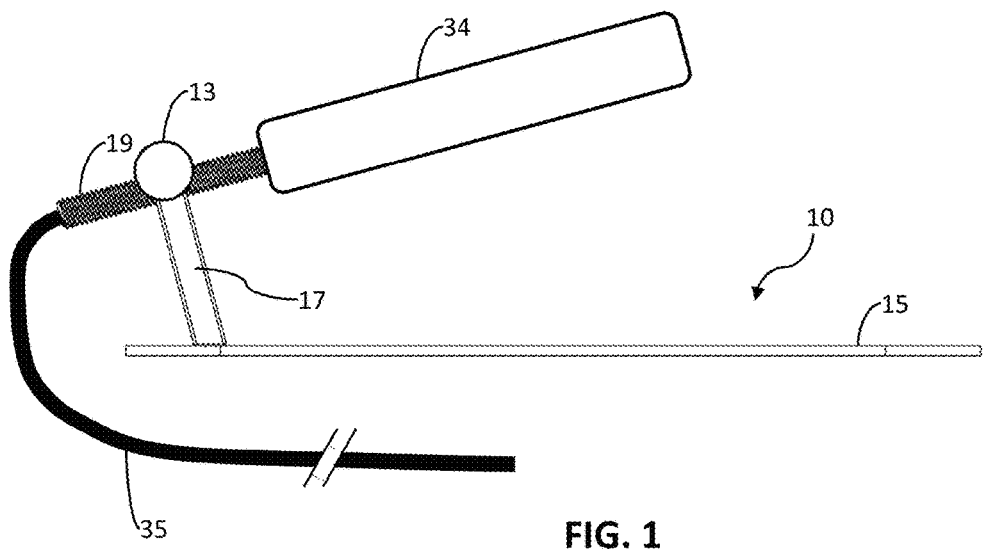
FIG. 1 shows side view of a stabilizer embodiment 10 with typical guide catheter 34.

At least one embodiment may allow adjustment and/or positioning of a medical device without requiring movement of the entire stabilizer system. In addition, certain embodiments can advantageously allow a portion of a medical device to be manipulated and/or repositioned relative to another portion of a medical device, where at least one embodiment does not require decoupling of the medical device from the stabilizer. Further, certain embodiments can advantageously hold and/or lock a medical device or a portion thereof in a desired position while preventing unintended and undesirable movement of the medical device FIG. 1 illustrates side view of a stabilizer embodiment 10. A schematic box is used to represent a guide catheter 34. For mitral valve procedures, a steerable guide catheter is typically used. In this exemplary embodiment 10, a threaded strain relief 19 is used. This strain relief is integral part of the guide catheter and is configured to have the required structural strength to support the catheter handle. The base components of the stabilizer 10 are composed of the base plate 15 and angled stabilizing post 17. Any of these components can be made of polymers, metals, alloys, reinforced composites, ceramics and/or their combinations that are of organic or inorganic in origin. For example, and not limited to this example, it can be made of PEEK, UHMWPE, Nylon, and/or Stainless Steel.

Figure 2:
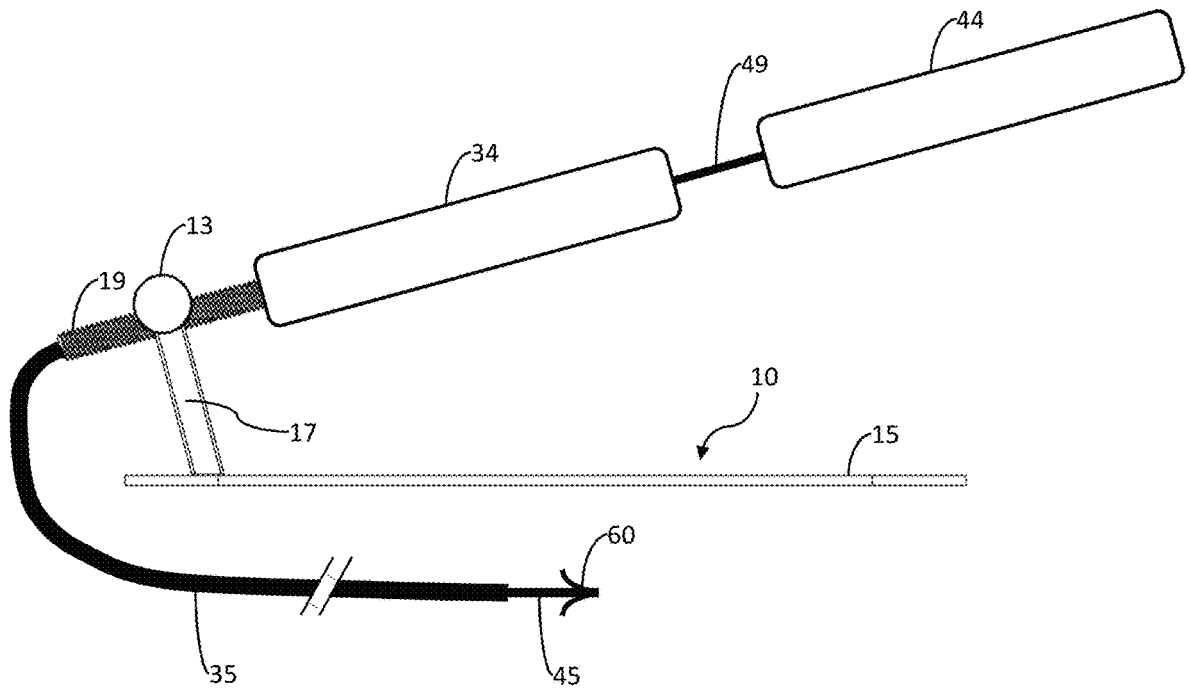
FIG. 2 shows side view of an exemplary stabilizer embodiment 10 with a typical guide catheter 34 and a delivery catheter 44.

FIG. 2 shows a delivery catheter used along with the stabilizer 10 and a guide catheter as described earlier in FIG. 1. This particular embodiment is used with delivery catheters 44, 45 that have structural proximal segment 49 that can be inserted inside the Guide handle for support. In such an exemplary embodiment, the structural proximal shaft 49 is reinforced with an elastic and/or rigid metal, polymer composite and/or ceramic material. Typically, the reinforced structural shaft 49 is inserted inside the guide catheter handle partially or up to and/or beyond the guide catheter structural strain relief 19.

Figure 3:
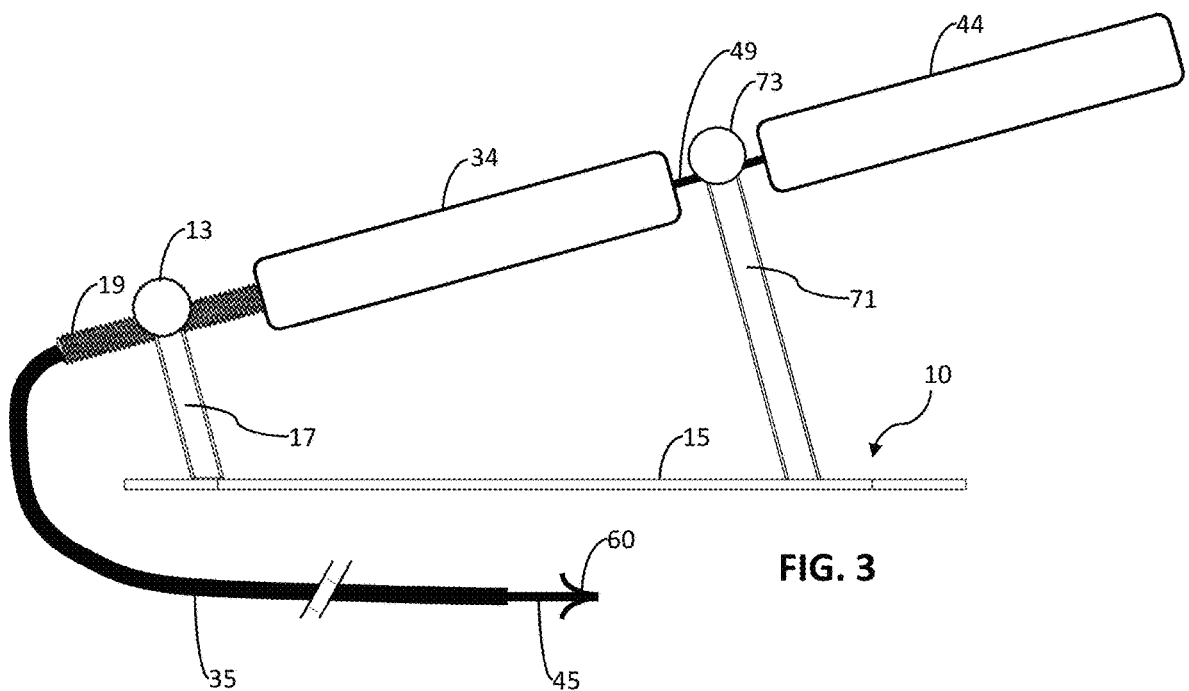
FIG. 3 shows side view of an exemplary stabilizer embodiment 10 with a typical guide catheter 34 and a delivery catheter 44. In addition, the stabilizer shows a second post 71 for added control and support for delivery catheter 44.

FIG. 3 shows an alternate embodiment of stabilizer 10, which comprises of additional and/or independent support post 71 for the delivery catheter 44. Further, all or most of the functional features (described in detail later in this invention) at post 17 for the guide catheter 34 via threaded strain relief 19 may be available and/or duplicated at post 71 for delivery catheter 44 via a similar structural strain relief 49. This second post 71 may be integral to base plate 10 or an independent secondary feature that can either be configured to be optionally attached to the base plate 10. For example, two or more independent stabilizers as shown in FIG. 1 may be used in tandem.

Figure 4:
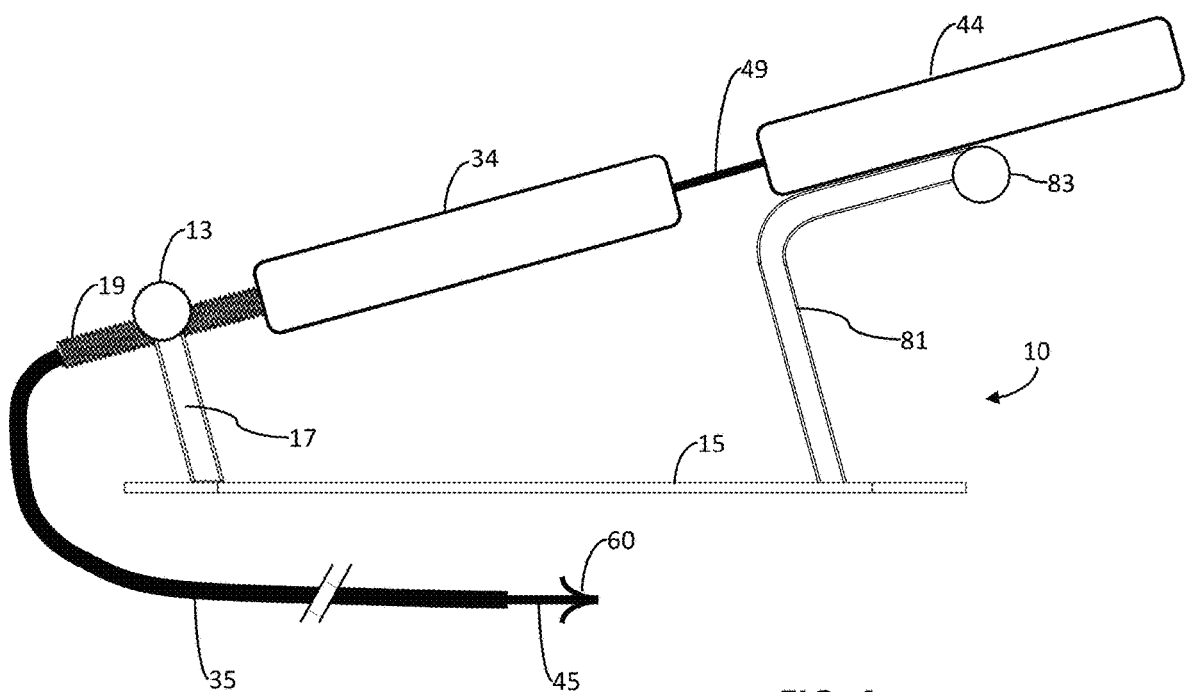
FIG. 4 shows side view of an exemplary stabilizer embodiment 10 with a typical guide catheter 34 and a delivery catheter 44. In addition, the stabilizer shows a second post 81 for added control and support for delivery catheter 44.

FIG. 4 shows an exemplary variation of embodiment 10, where the delivery catheter is supported and controlled by a curved post 81. In this configuration, structural reinforcement of proximal shaft 49 is optional. Further, the rotational and translational motion of the delivery catheter 44 can be controlled using a knob 83 or any design that is commonly used in engineering.

Figure 5:
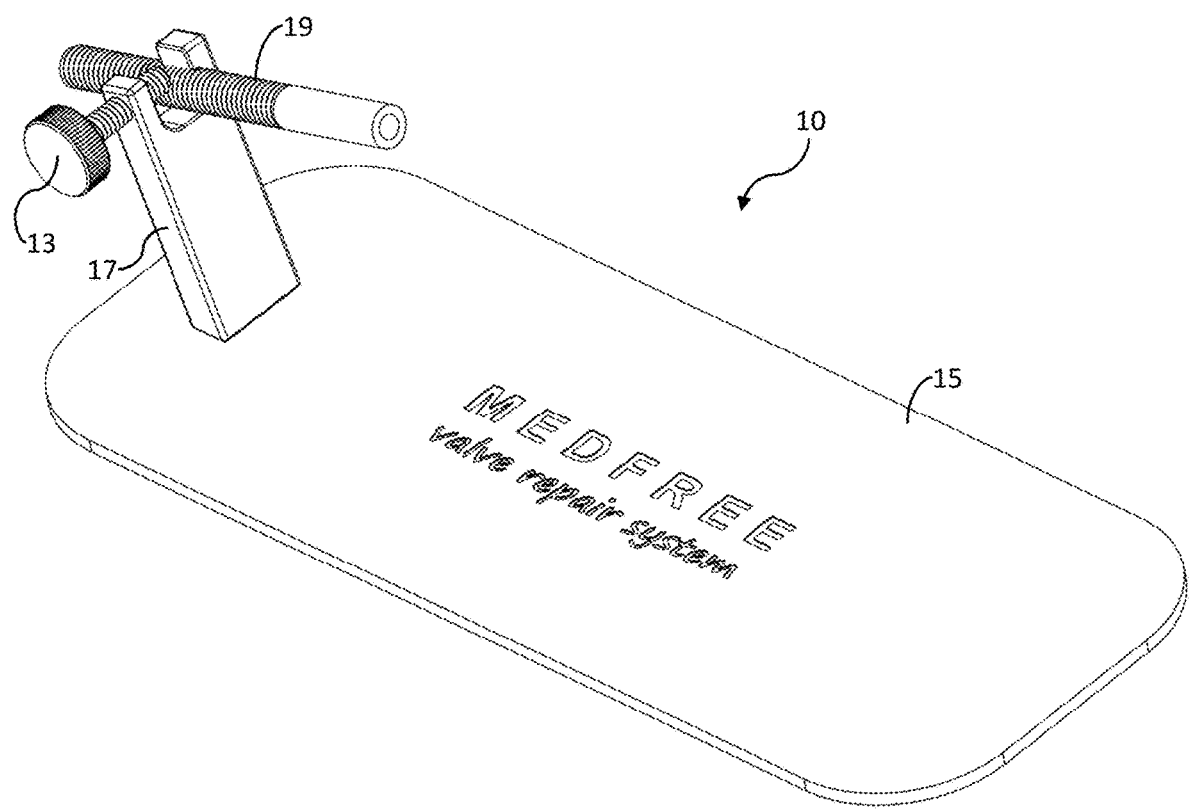
FIG. 5 shows a 3D view of the exemplary stabilizer embodiment 10. It additionally shows a representative and exemplary guide catheter interfacing component 19.

FIG. 5 shows 3D view of the stabilizer embodiment 10, as shown in FIG. 1. The guide catheter body is not shown for simplicity, instead, it is represented via the threaded strain relief 19.

Figure 6:
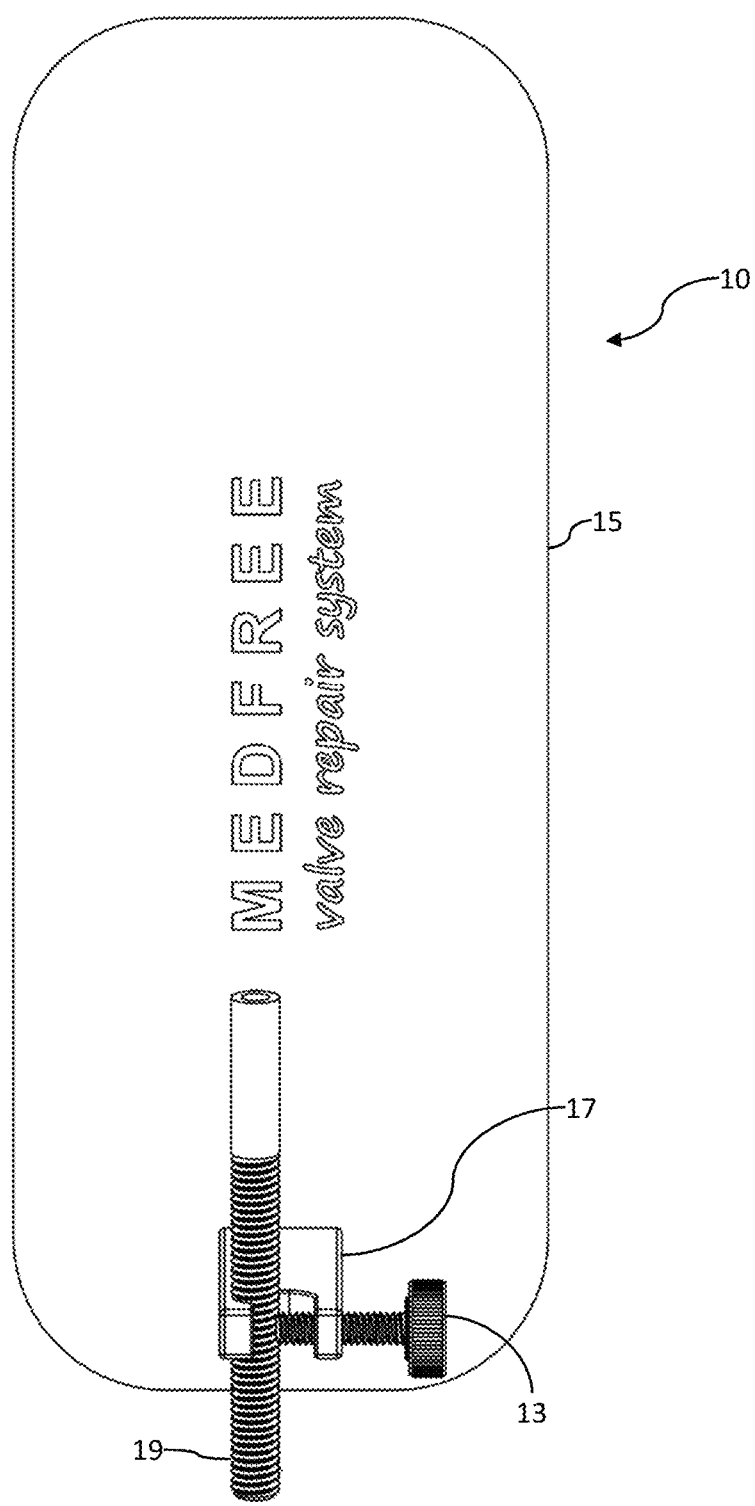
FIG. 6 shows a top view of the exemplary stabilizer embodiment 10, as shown in FIG. 5.

FIG. 6 shows the top view of the exemplary stabilizer embodiment 10 shown earlier in FIG. 5.

Figure 7:
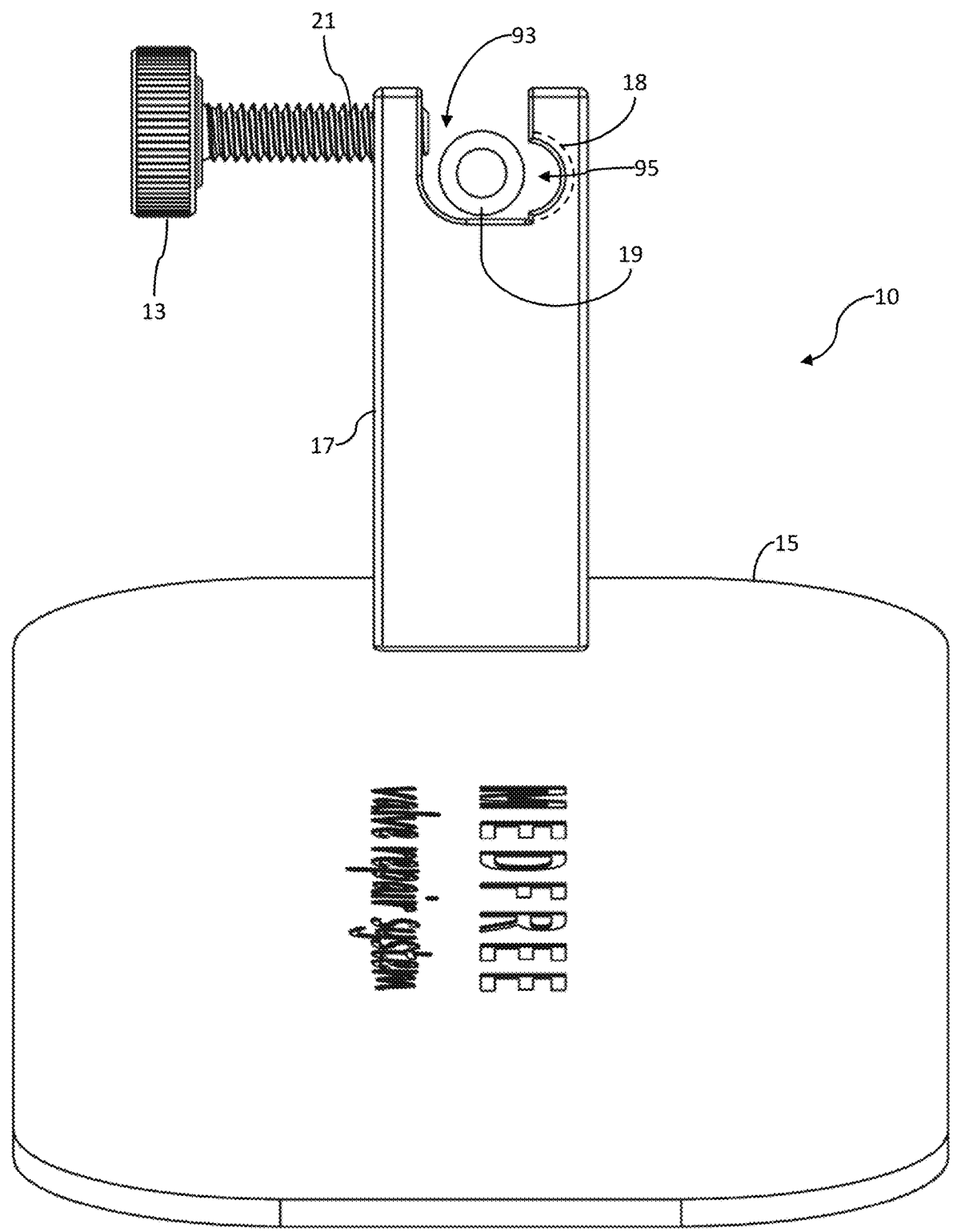
FIG. 7 shows a 3D back view of the exemplary stabilizer embodiment 10, as shown in FIG. 5 and configured to allow for controlled rotational as well as translational motion of the catheter 19. In this configuration, it is also optionally possible to remove (or engage) the catheter with the stabilizer 10

FIG. 7 shows an exemplary configuration of the stabilizer embodiment 10 that was shown earlier in FIG. 5. As can be noted in this configuration, Knob 13 is fully retracted and there is a large gap 93 between the threaded strain relief 19 and knob screw 21. Additionally, there is also a large gap 95 between the threaded strain relief 19 and the tapped/threaded region 18 of the post 17. Thus, in this configuration, the threaded strain relief 19 can be translated as well as rotated. These motions can be performed by the user by directly grasping the guide handle 34 and moving it, thus preserving the desired tactile feedback. Additionally, in this configuration, it is also possible to remove/disengage (or insert/ engage) the catheter 19 with the stabilizer 10.

Figure 8:
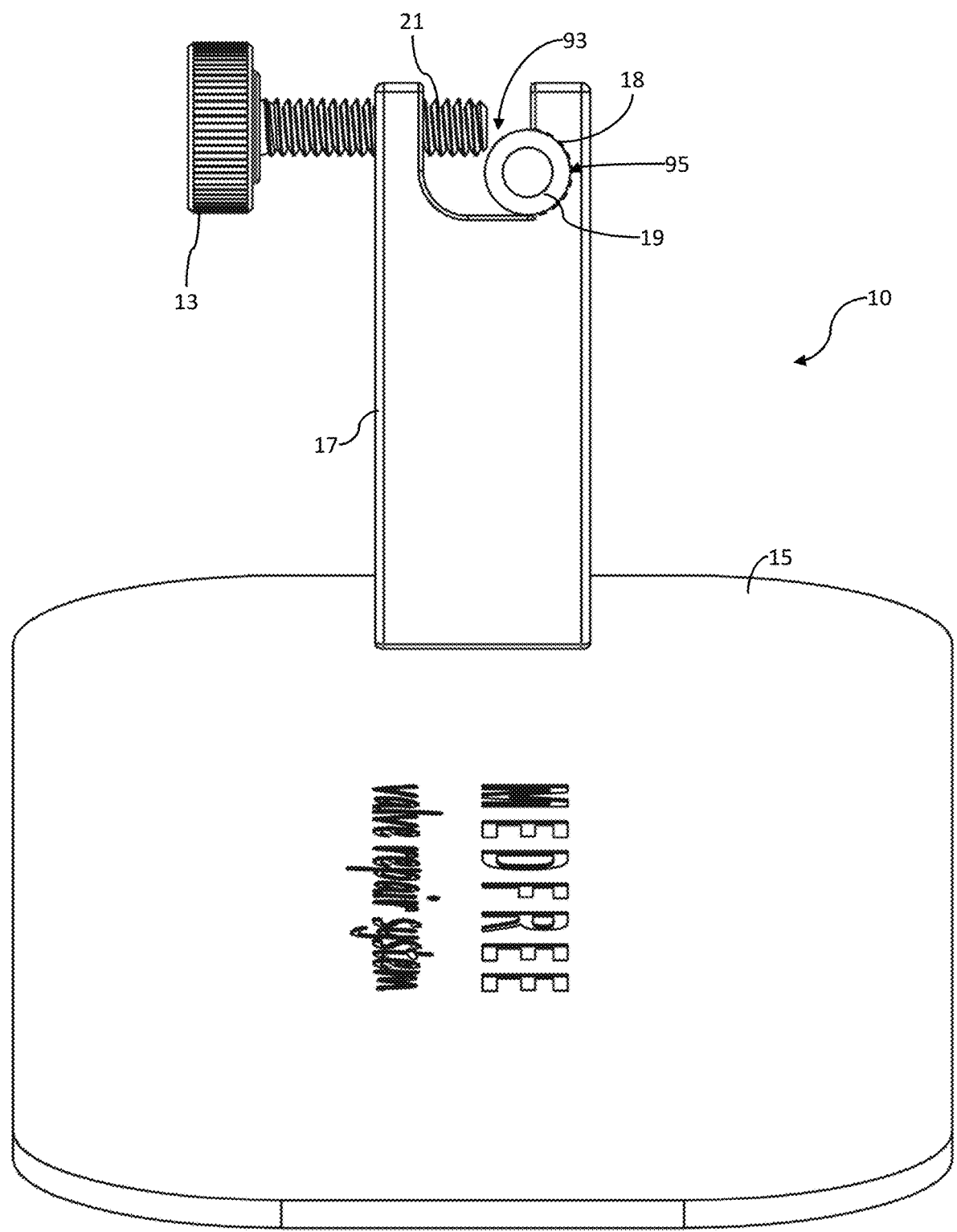
FIG. 8 shows a 3D back view of the exemplary stabilizer embodiment 10, as shown in FIG. 5 and configured to allow for controlled rotational motion of the catheter 19 while restricting the translation.

FIG. 8 shows an exemplary configuration of the stabilizer embodiment 10 that was shown earlier in FIG. 5. As can be noted in this configuration, Knob 13 is partially closed and there is a small gap 93 between the threaded strain relief 19 and knob screw 21. Additionally, there is no gap 95 between the threaded strain relief 19 and the tapped/threaded region 18 of the post 17. Thus, as is evident in this configuration, the threaded strain relief 19 can be rotated, however, it cannot be translated axially (with any clinical significance). This rotational motion can be performed by the user by directly grasping the guide handle 34 and rotating it, thus preserving the desired tactile feedback.

Figure 9:
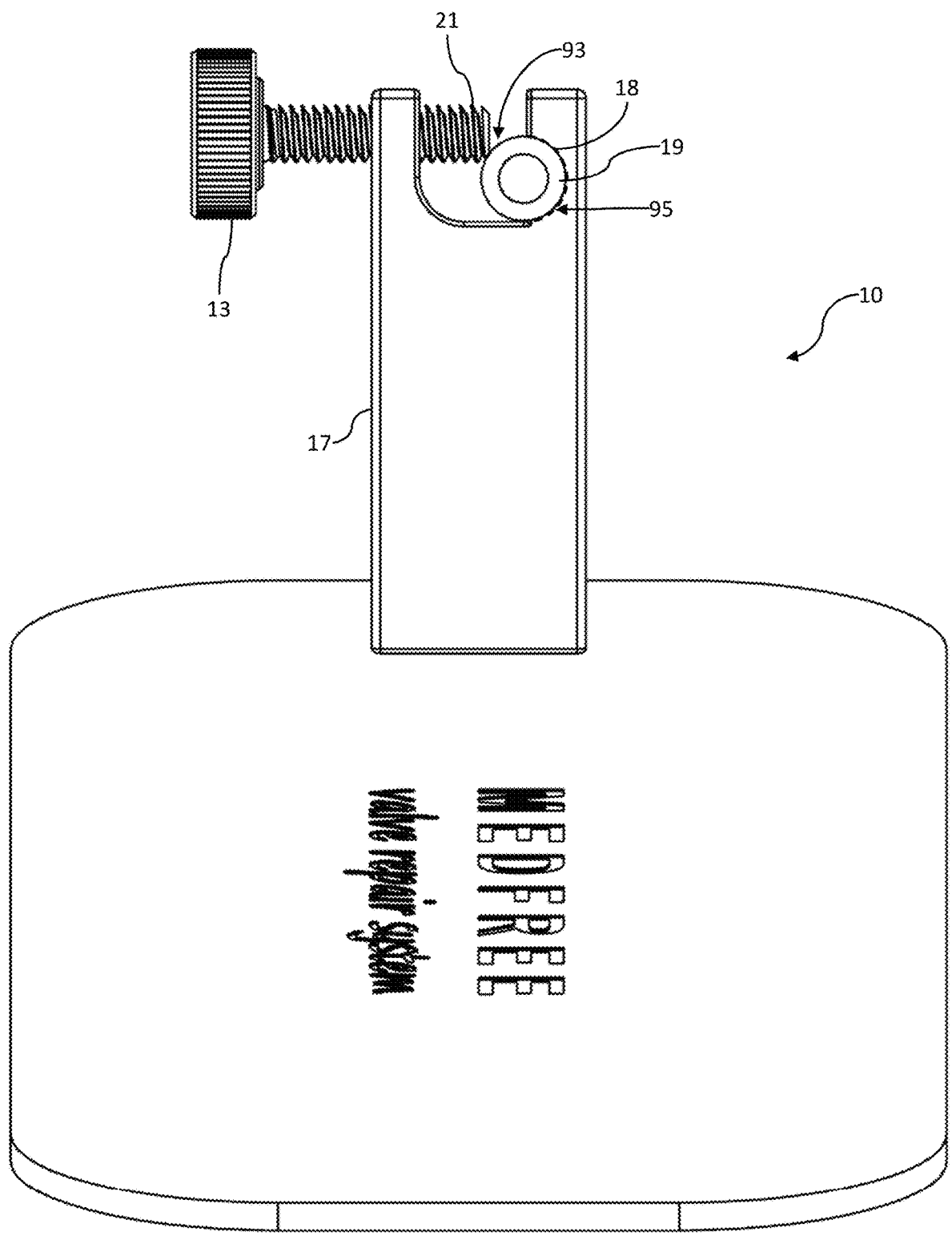
FIG. 9 shows a 3D back view of the exemplary stabilizer embodiment 10, as shown in FIG. 5. Additionally, the FIG. 9 shows a configuration where the catheter is fixed in position by the knob 13.

FIG. 9 shows an exemplary configuration of the stabilizer embodiment 10 that was shown earlier in FIG. 5. As can be noted in this configuration, there is no gap 93 between the threaded strain relief 19 and knob screw 21. That is, the Knob 13 is fully closed and tightened on to the threaded strain relief 19, which in turn is fully meshed into the taped region 18. Thus, as is evident, there is complete restriction of both rotation and translation of the threaded strain relief 19. That is, in this configuration, the guide catheter is fixed in the set position relative to the stabilizer 10.

Figure 10:
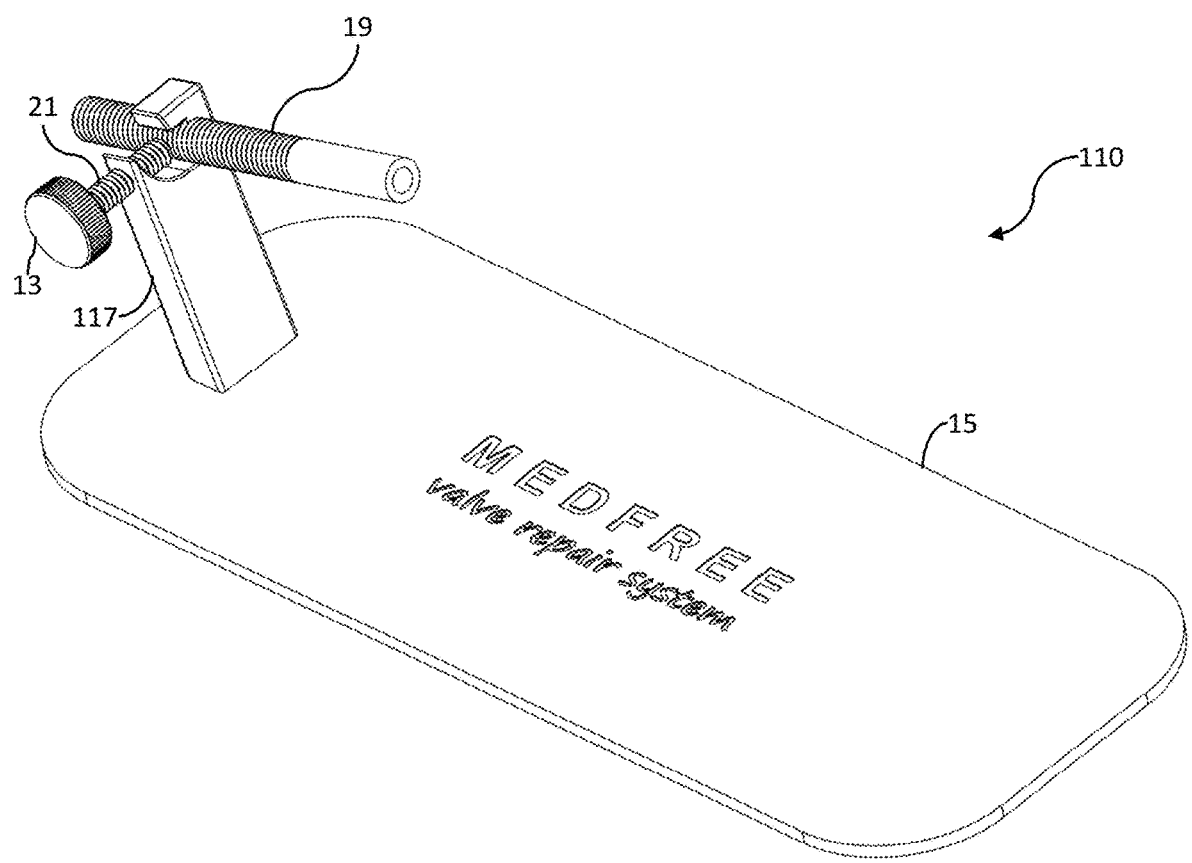
FIG. 10 shows a 3D view of an alternate exemplary stabilizer embodiment 110. It additionally shows a representative and exemplary guide catheter interfacing component 19.
Figure 11:
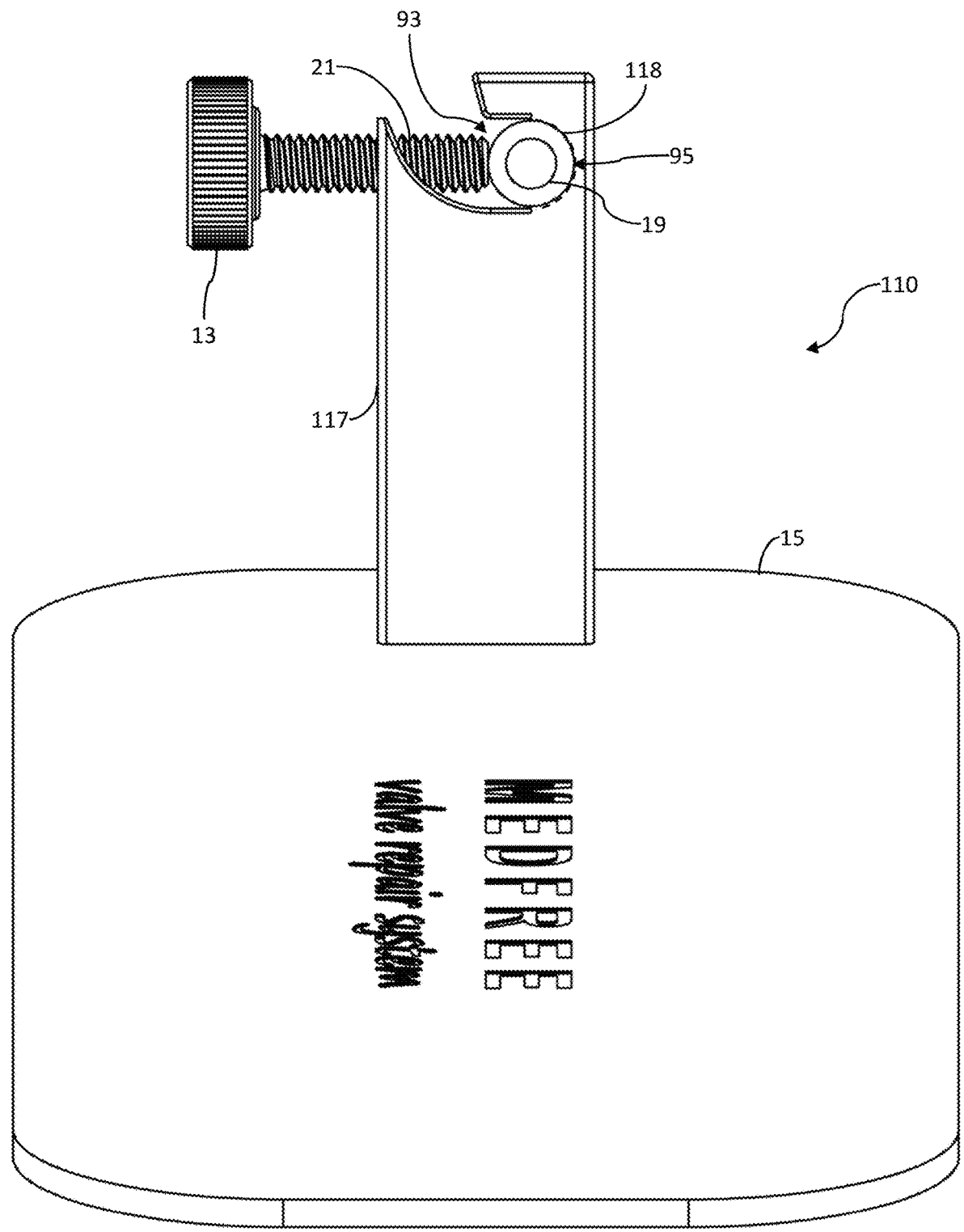
FIG. 11 shows a 3D back view of the exemplary stabilizer embodiment 110, as shown in FIG. 10. Additionally, the FIG. 11 shows a configuration where the catheter is fixed in position by the knob 13.

FIG. 10 shows a 3D view of an alternate exemplary stabilizer embodiment 110. It additionally shows a representative and exemplary guide catheter interfacing component comprising of a threaded strain relief 19. The primary difference from stabilizer embodiment 10 is in the design of the post 117, which better evident in FIG. 11.

Figure 12:
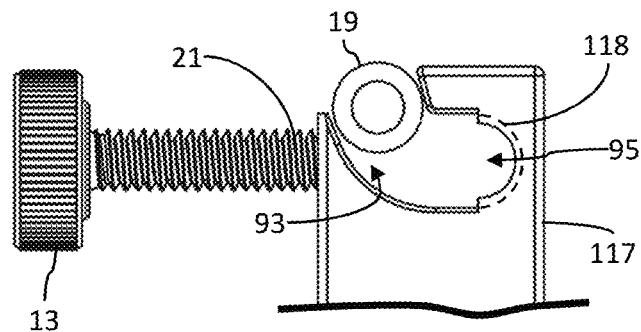
FIG. 12 shows a cropped back view of the exemplary stabilizer embodiment 110, as shown in FIG. 10. In this configuration, the knob 13 is unscrewed all the way back, hence, it is possible to remove (or attach/engage) the catheter with the stabilizer 110.

FIG. 12 shows a cropped back view of the exemplary stabilizer embodiment 110, as shown in FIG. 10. In this configuration, the threaded strain relief can be removed or engaged with the stabilizer 110.

Figure 13:
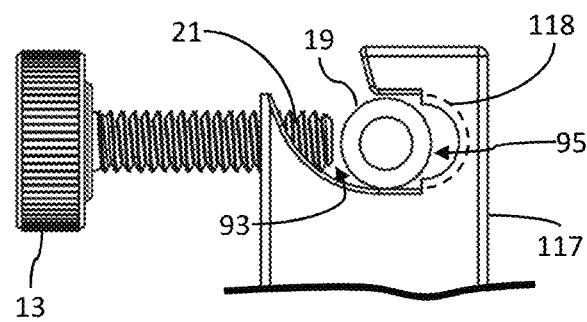
FIG. 13 shows a cropped back view of the exemplary stabilizer embodiment 110, as shown in FIG. 10, wherein, the knob 13 is partially screwed in a configuration that allows for controlled rotational as well as translational motion of the catheter 19.

FIG. 13 shows a cropped back view of the exemplary stabilizer embodiment 110, as shown in FIG. 10. As can be noted in this configuration, Knob 13 is fully retracted and there is a large gap 93 between the threaded strain relief 19 and knob screw 21. Additionally, there is also a large gap 95 between the threaded strain relief 19 and the tapped/threaded region 118 of the post 117. Thus, in this configuration, the threaded strain relief 19 can be translated as well as rotated. These motions can be performed by the user by directly grasping the guide handle 34 and moving it, thus preserving the desired tactile feedback. Additionally, in this configuration, it is also possible to remove/disengage (or insert/ engage) the catheter 19 with the stabilizer 110.

Figure 14:
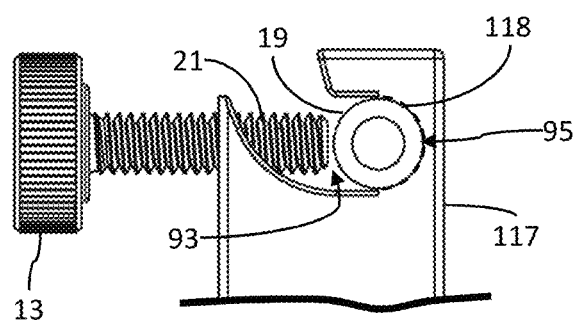
FIG. 14 shows a cropped back view of the exemplary stabilizer embodiment 110, as shown in FIG. 10, wherein, the knob 13 is partially screwed in a configuration that allows for controlled rotational motion of the catheter 19 while restricting the translation. This, as the catheter shaft 19 engages with the threads 118.

FIG. 14 shows an exemplary configuration of the stabilizer embodiment 110 that was shown earlier in FIG. 10. As can be noted in this configuration, Knob 13 is partially closed and there is a small gap 93 between the threaded strain relief 19 and knob screw 21. Additionally, there is no gap 95 between the threaded strain relief 19 and the tapped/ threaded region 118 of the post 117. Thus, as is evident in this configuration, the threaded strain relief 19 can be rotated, however, it (essentially) cannot be translated. This rotational motion can be performed by the user by directly grasping the guide handle 34 and rotating it, thus preserving the desired tactile feedback.

Figure 15:
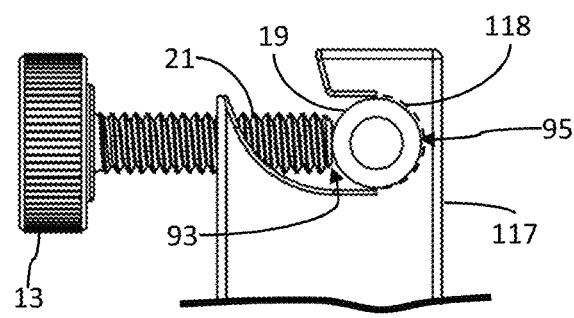
FIG. 15 shows a cropped back view of the exemplary stabilizer embodiment 210. Additionally, it shows a configuration where the catheter 19 fixed in position. This, as the knob 13 is fully screwed in and tightened on to the catheter shaft 19.

FIG. 15 shows an exemplary configuration of the stabilizer embodiment 110 that was shown earlier in FIG. 10. As can be noted in this configuration, there is no gap 93 between the threaded strain relief 19 and knob screw 21. That is, the Knob 13 is fully closed and tightened on to the threaded strain relief 19, which in turn is fully meshed into the tapped/threaded region 118. Thus, as is evident, there is complete restriction of both rotation and translation of the threaded strain relief 19. That is, in this configuration, the guide catheter is fixed in the set position relative to the stabilizer 110.

Figure 16:
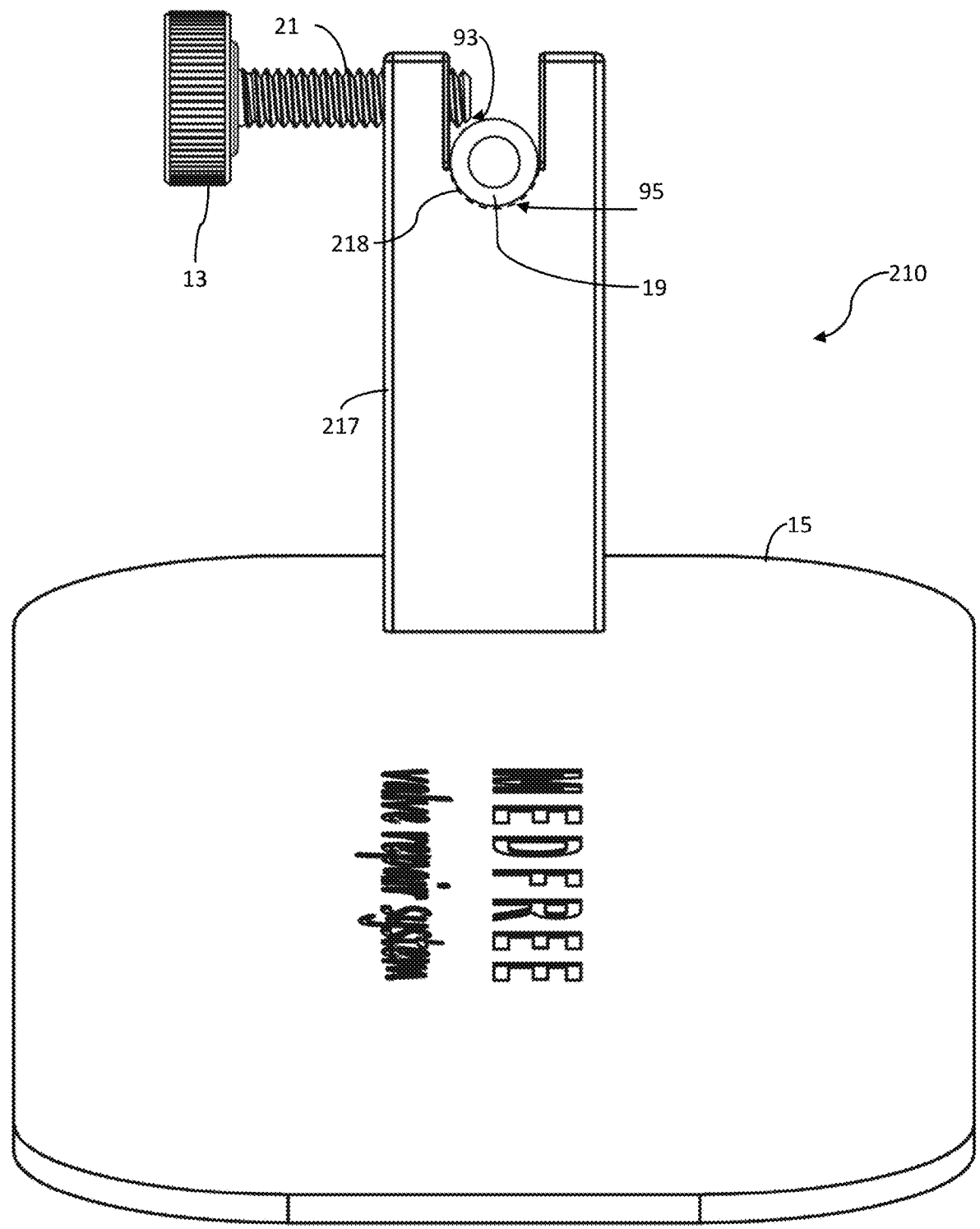
FIG. 16 shows a 3D back view of the exemplary stabilizer embodiment 210, wherein, the knob 13 is in an exemplary configuration that to allows for controlled rotational motion of the catheter 19 while restricting the translation.

FIG. 16 shows a 3D back view of the exemplary stabilizer embodiment 210, wherein, the knob 13 is in an exemplary configuration that to allows for controlled rotational motion of the catheter 19 while restricting the translation.

Figure 17:
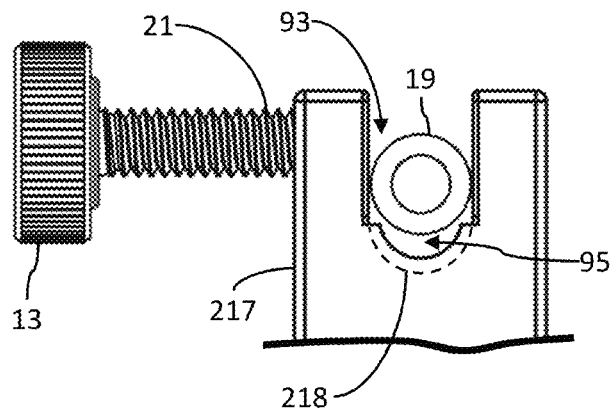
FIG. 17 shows a cropped back view of the exemplary stabilizer embodiment 210, as shown in FIG. 16, wherein, the knob 13 is in an exemplary configuration that allows for controlled rotational as well as translational motion of the catheter 19. In this configuration, the knob 13 is unscrewed all the way back, hence, it is possible to remove (or attach/engage) the catheter with the stabilizer 210.

FIG. 17 shows a cropped back view of the exemplary stabilizer embodiment 210, as shown in FIG. 16. In this configuration, the threaded strain relief can be removed or engaged with the stabilizer 210. Further, as can be noted in this configuration, Knob 13 is fully retracted and there is a large gap 93 between the threaded strain relief 19 and knob screw 21. Additionally, there is also a large gap 95 between the threaded strain relief 19 and the tapped/threaded region 218 of the post 217. Thus, in this configuration, the threaded strain relief 19 can be translated as well as rotated. These motions can be performed by the user by directly grasping the guide handle 34 and moving it, thus preserving the desired tactile feedback. Additionally, in this configuration, it is also possible to remove/disengage (or insert/engage) the catheter 19 with the stabilizer 10.

Figure 18:
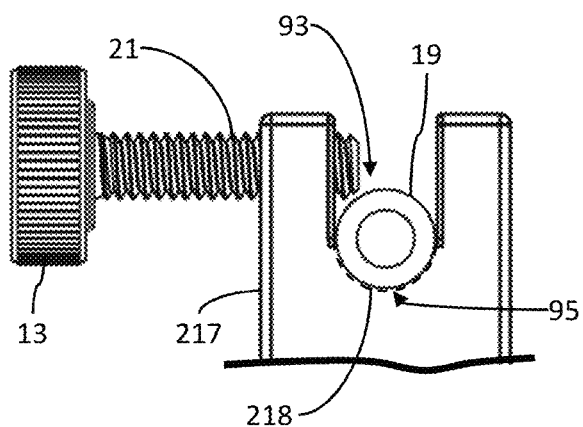
FIG. 18 shows a cropped back view of the exemplary stabilizer embodiment 210, as described in FIG. 17, wherein, the knob 13 is partially screwed in a configuration that allows for controlled rotational motion of the catheter 19 while restricting the translation.

FIG. 18 shows an exemplary configuration of the stabilizer embodiment 210 that was shown earlier in FIG. 16. As can be noted in this configuration, Knob 13 is partially closed and there is a small gap 93 between the threaded strain relief 19 and knob screw 21. Additionally, there is no gap 95 between the threaded strain relief 19 and the tapped/ threaded region 218 of the post 217. Thus, as is evident in this configuration, the threaded strain relief 19 can be rotated, however, it cannot be translated. This rotational motion can be performed by the user by directly grasping the guide handle 34 and rotating it, thus preserving the desired tactile feedback.

Figure 19:
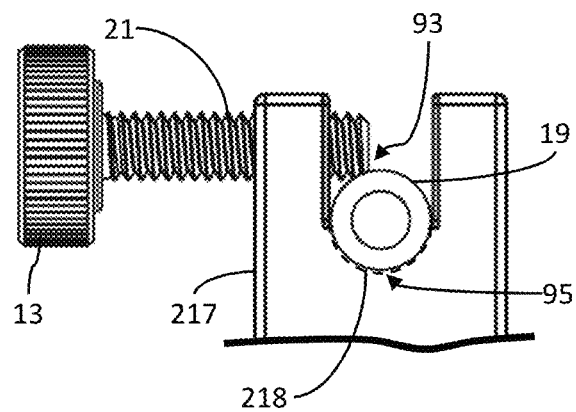
FIG. 19 shows a cropped back view of the exemplary stabilizer embodiment 210, as shown in FIG. 16. Additionally, it shows a configuration where the catheter 19 fixed in position. This, as the knob 13 is fully screwed in and tightened on to the catheter shaft 19.

FIG. 19 shows an exemplary configuration of the stabilizer embodiment 210 that was shown earlier in FIG. 16. As can be noted in this configuration, there is no gap 93 between the threaded strain relief 19 and knob screw 21. That is, the Knob 13 is fully closed and tightened on to the threaded strain relief 19, which in turn is fully meshed into the tapped/threaded region 218. Thus, as is evident, there is complete restriction of both rotation and translation of the threaded strain relief 19. That is, in this configuration, the guide catheter is fixed in the set position relative to the stabilizer 210.

Figure 20:
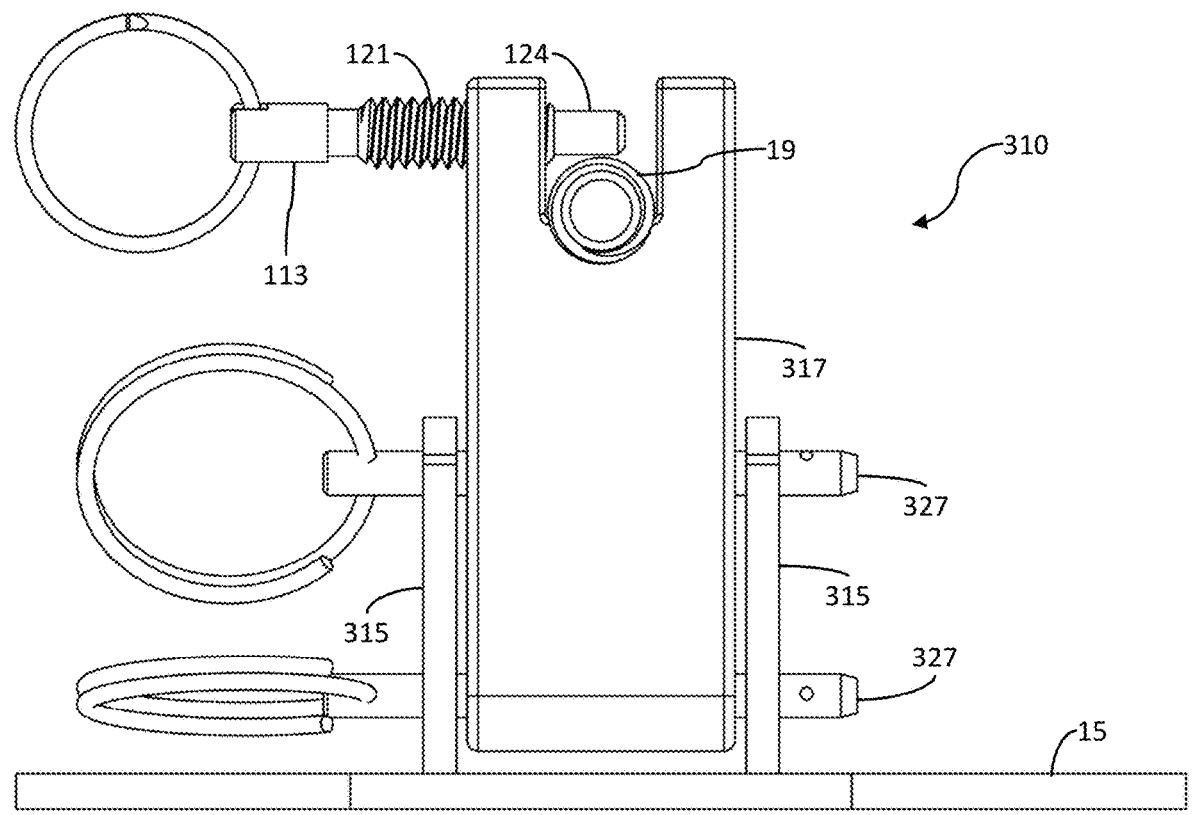
FIG. 20 shows a 3D front view of an alternate exemplary stabilizer embodiment 310 in an exemplary configuration that allows for controlled rotational motion of the catheter 19 while restricting the translation. It uses a retractable spring plunger for quick actuation. Further, it uses a swiveling post 317 to allow various angles of catheter shaft (represented by catheter shaft threaded strain relief 19).

FIG. 20 shows a 3D front view of an alternate exemplary stabilizer embodiment 310 and configured to allow for controlled rotational motion of the catheter 19 while restricting the translation. It uses a retractable spring plunger 113 for quick actuation. Further, it uses a swiveling post 317 to allow various angles of the guide catheter (not shown for simplicity and is represented by threaded strain relief 19).

Figure 21:
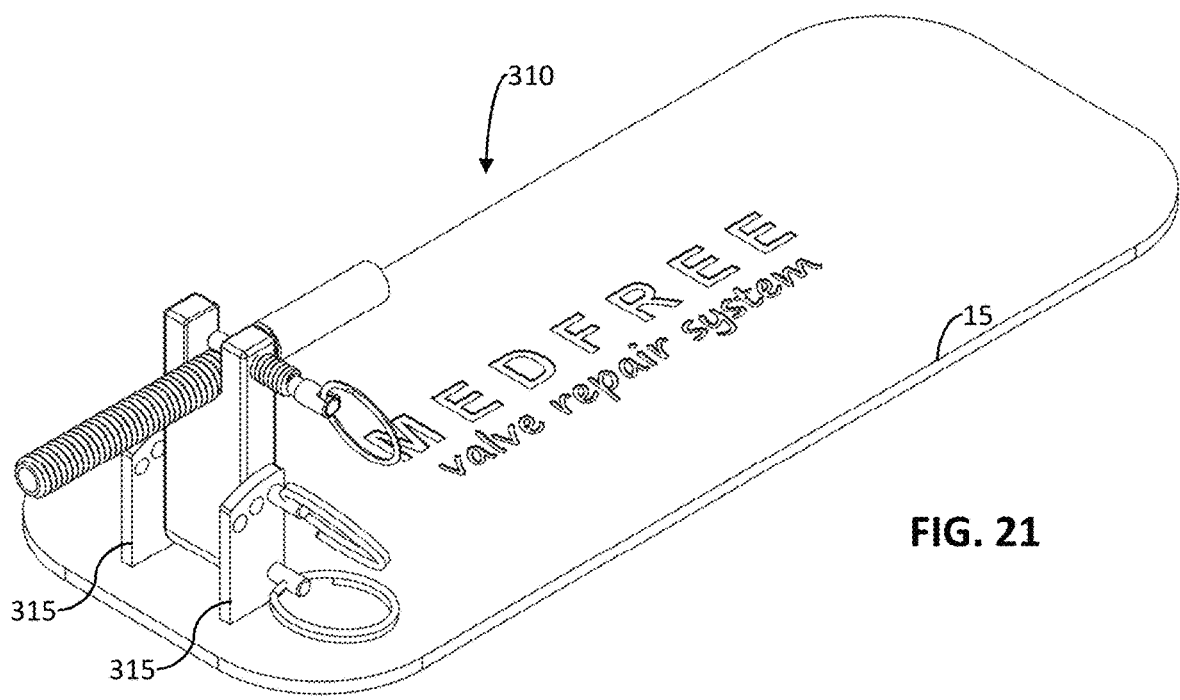
FIGS. 21-22 show 3D side views of the stabilizer 310.
Figure 22:
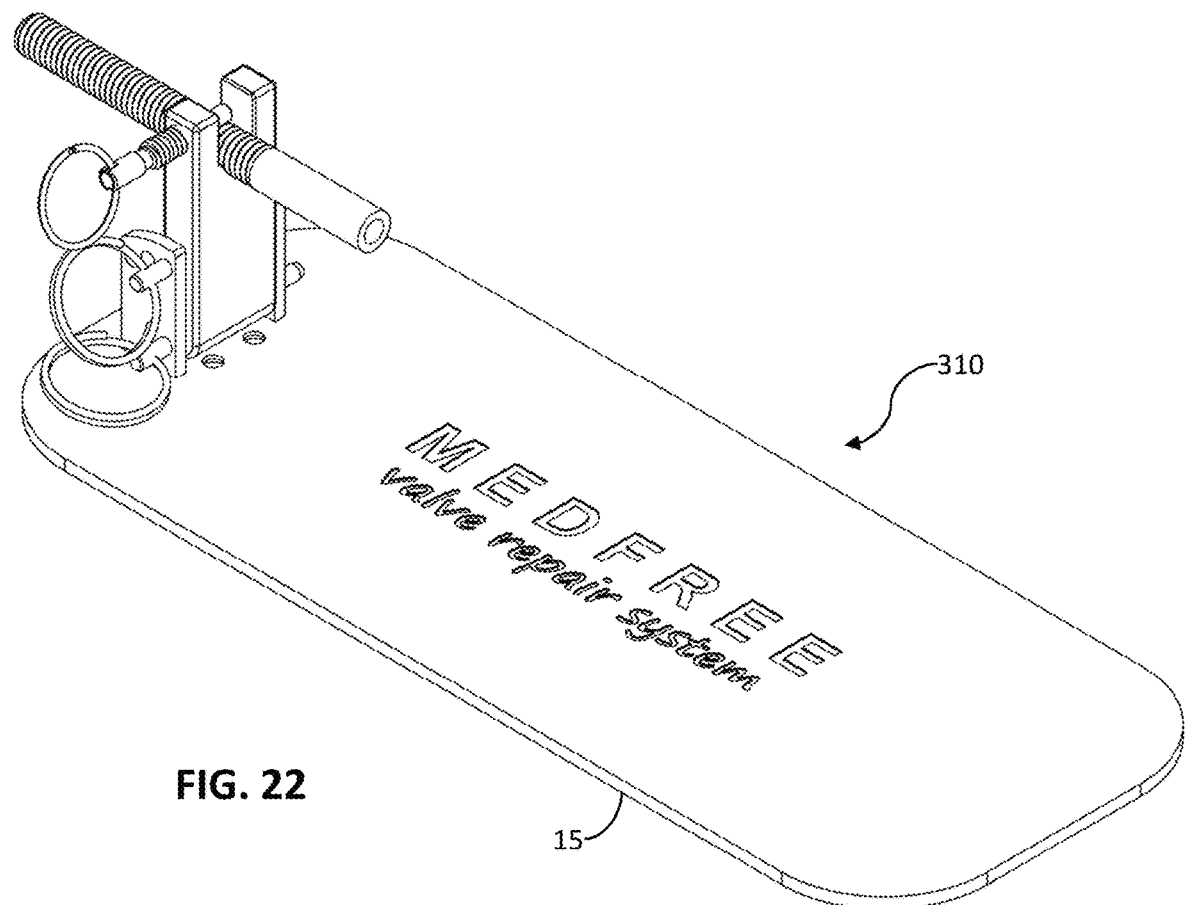
Figure 23:
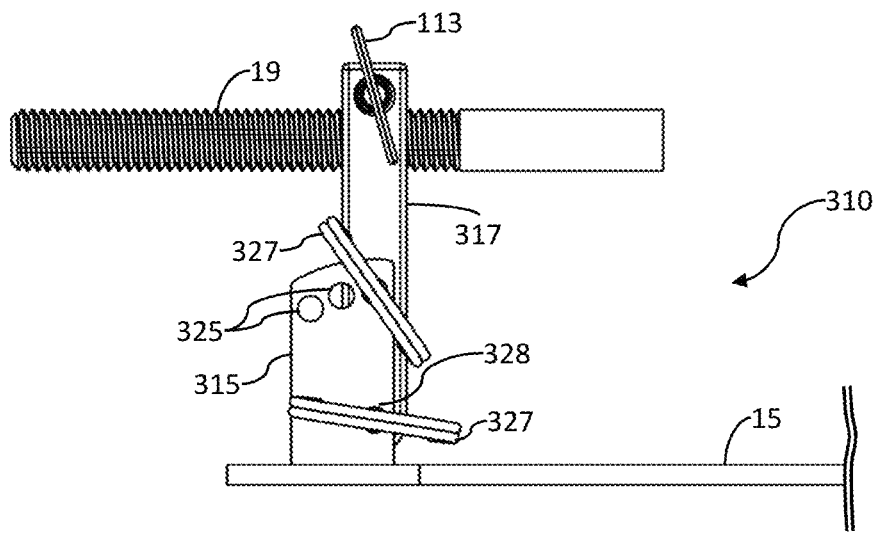
FIGS. 23-25 show 3D side view of the stabilizer 310 in 3 different angle configurations of the catheter (represented by threaded strain relief 19).
Figure 24:
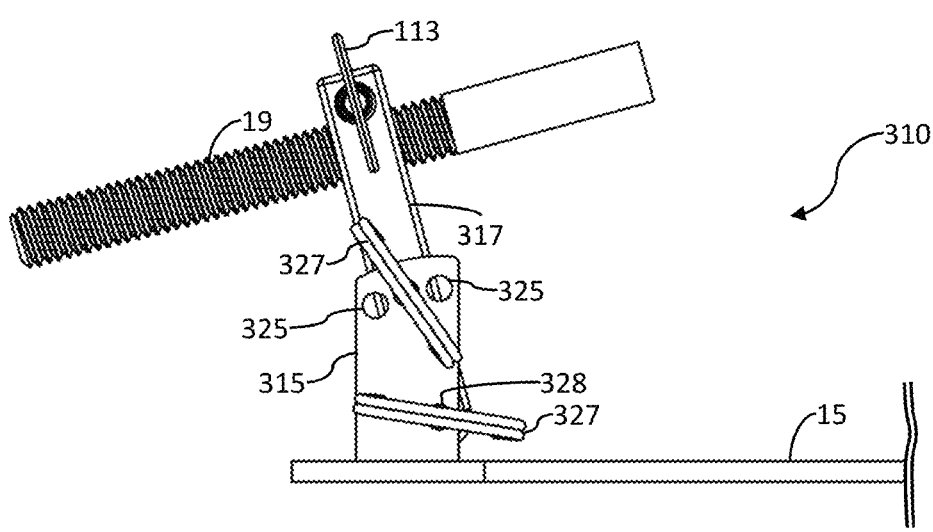
Figure 25:
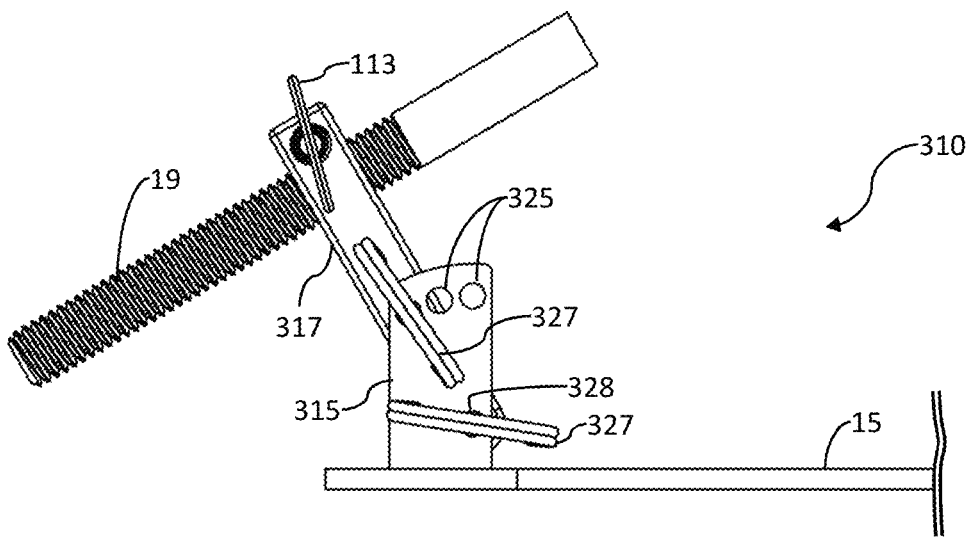

FIGS. 21-22 show 3D side views of the stabilizer 310. As can be seen in FIGS. 20-23, there are two plates 315. Each of these plates 315 have a bottom hole 328 that is used as a hinge about which the swiveling stabilizer post 317 rotates. This is achieved by assembling the swiveling post 317 through the bottom hole 328 using a quick connect pin 327. Next, the swiveling post 317 is set at a desired angle using one of the three available top holes 325 by inserting a second quick connect pin 327. FIGS. 23-25 show three such exemplary configurations using each of the three top holes 325.

Figure 26:
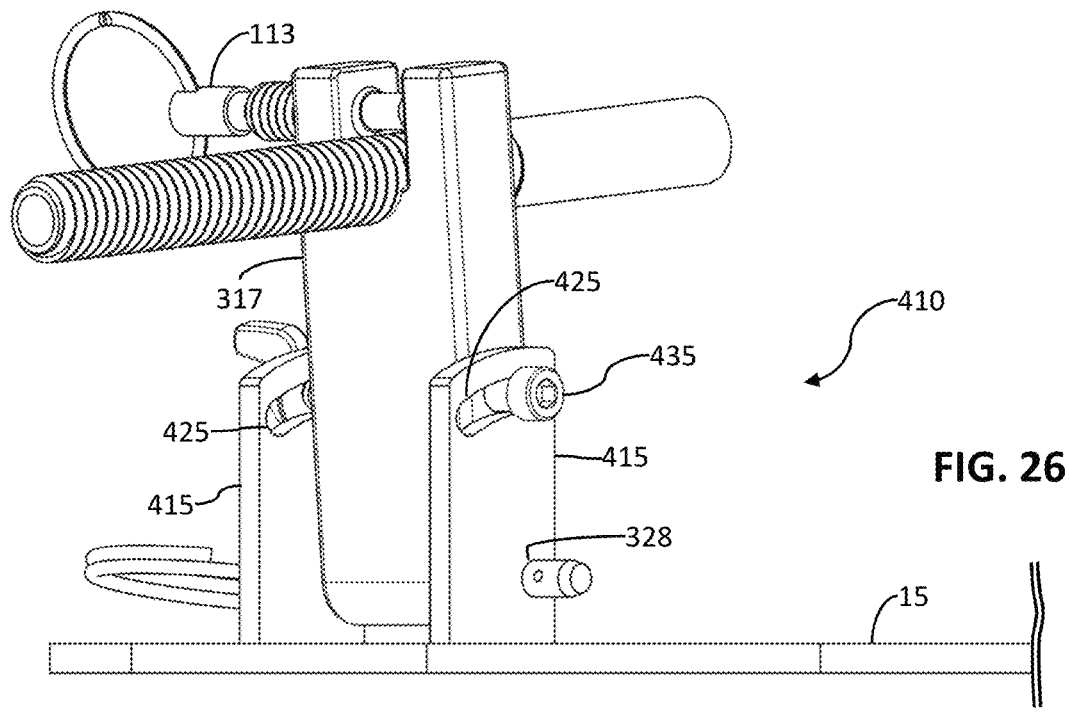
FIGS. 26-27 show cropped 3D views of an exemplary embodiment 410 with slotted plates 415 that allow for a range of smooth variations in the angle of the catheter—as represented by threaded strain relief 19.
Figure 27:
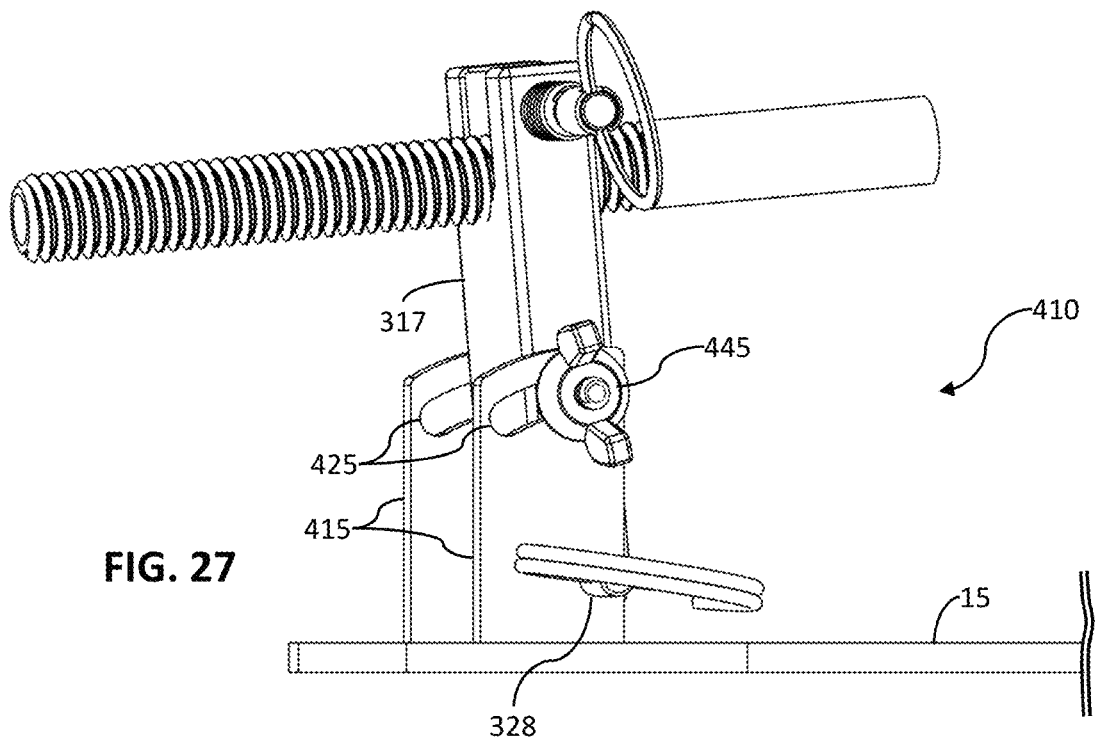

FIGS. 26-27 show cropped 3D views of an exemplary embodiment 410 with slotted plates 415 that allow for a range of smooth variations in the angle of the catheter—as represented by threaded strain relief 19. Instead of using quick connect pins through top holes 325 shown previously in FIGS. 20-25, a screw 435 and a wing-nut 445 is used to lock the swiveling post 317 at a desired location within the slot 425.

Figure 28:
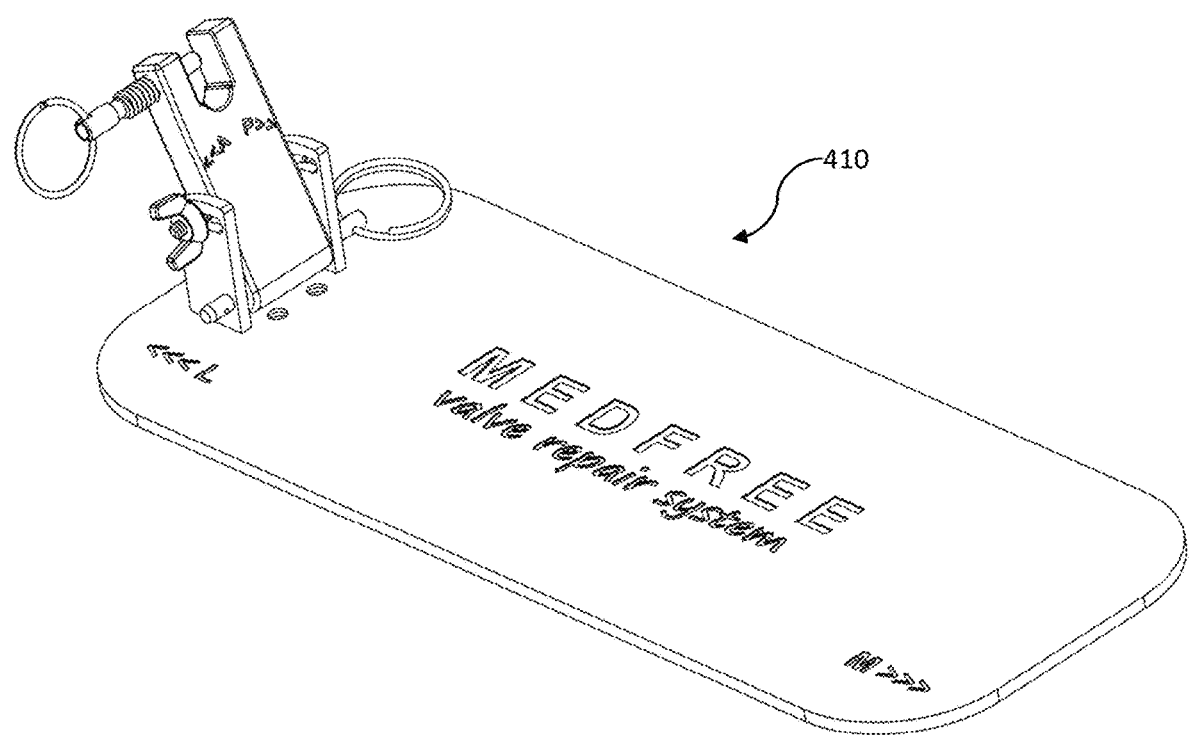
FIG. 28 shows exemplary embodiment 410 with labels M, L, A, P with arrows.

FIG. 28 shows exemplary embodiment 410 with labels M, L, A, P with arrows. Although the labels shown in the FIG. 28 are debossed, any other means obvious to those in medical device industry or manufacturing industry may be use. A few examples and not limited to these examples are laser etching, molding, stamping, engraving and/or powder coating.

Figure 29:
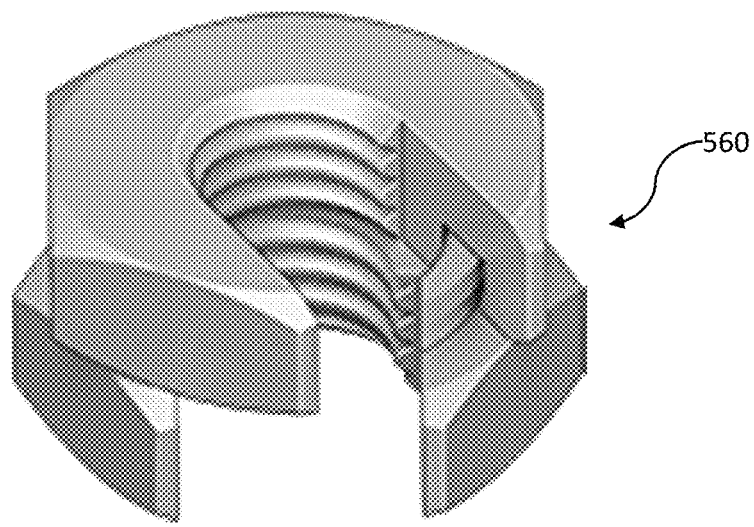
FIGS. 29-30 show alternate methods of quick engaging and dis-engaging of the threaded strain relief 19 with the stabilizer.
Figure 30:
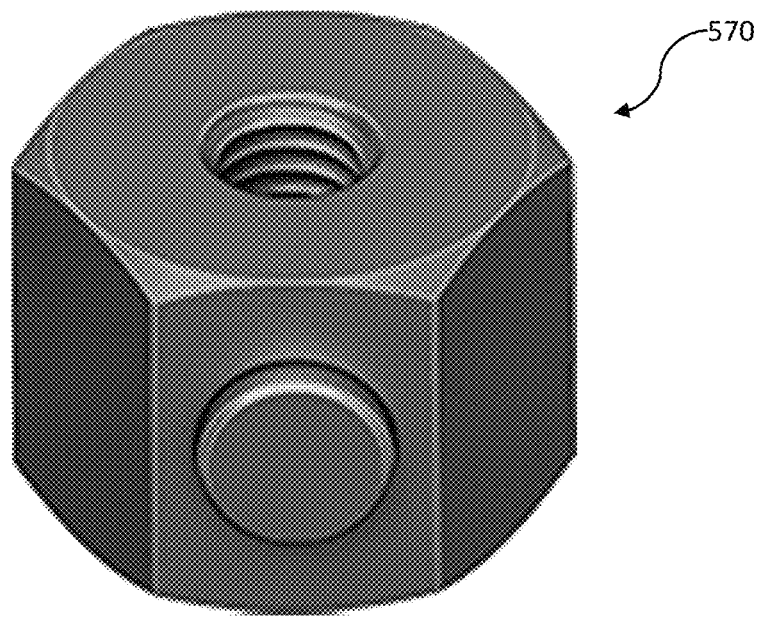

FIGS. 29-30 show alternate means of quickly engaging/locking and/or disengaging/unlocking the threaded strain relief 19 with the stabilizer. For example, a Slip-on twist-close nut 560 or Hex Push-Button Slide-Adjust Nut 570 may be attached to the exemplary stabilizer post 217, instead of using tapped/threaded segment 218 in conjunction with knob 13 (containing screw 21) to control manipulation of the threaded strain relief 19.

In an alternate exemplary embodiment, a mechanism such as Hex Push-Button Slide-Adjust Nut 570 may be incorporated inside the proximal guide handle 34. The strain relief 49 of delivery handle 44, can be configured to comprise gripping features such as ribs or threads (similar to guide catheter threaded strain relief 19). The push button or actuating mechanism of the nut 570 can be configured in open/close and various other intermediate positions. In open position, the threaded strain relief 49 can be inserted, removed, rotated and/or translated relative to the guide catheter. In an intermediate position, the threaded strain relief 49 can be rotated but not translated. In closed position, the threaded strain relief 49 (and hence, the delivery catheter handle 44) can be fixed in position and rotation relative to the guide catheter handle 34. Alternatively and additionally, a hemostasis valve may be incorporated into the guide handle 34, to accomplish the previously described motion constraints of the delivery catheter handle 44 and provide hemostasis in an exemplary configuration as shown in FIG. 2. While a threaded strain relief (or lead screw) was described as an example, the previously described gripping and motion actuation may be achieved using ribs, slots, directional and/or non-directional frictional features, commonly known to those skilled in the art.

Figure 31:
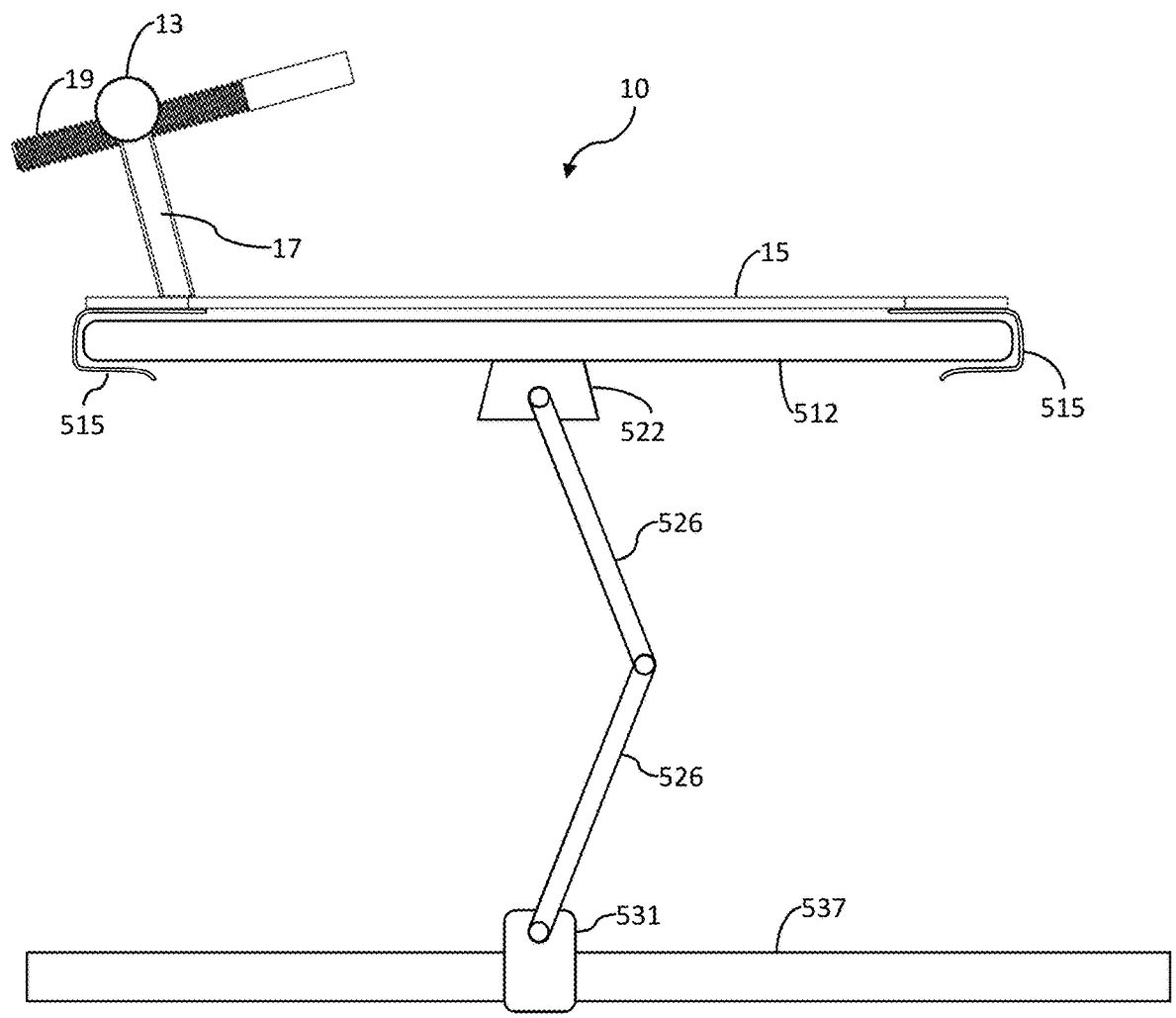
FIG. 31 shows an exemplary stabilizer 10 securely clamped to the OR table tray 512. The OR table tray 512 is mounted on to the standard side rail 537 of the OR table via lockable articulating arms 526.

FIG. 31 shows an exemplary stabilizer embodiment 10 is configured to be mated and securely mounted on to an articulated tray 512 and/or a receptacle 522. The articulated system may be lockable and/or re-positionable to provide a stable and secure platform for mounting the stabilizer. Further, the articulated (or alternatively bendable/malleable) system may be removably mounted on the standard side rails of the Operating Table or placed on a floor or table stand. Alternatively, the stabilizer may be placed on a floor stool or OR table stool. Further, the stool may have adjustable height and incline.

Embodiments described here are exemplary only and other variations quite evident to those skilled in the art are hence included herein. For example, instead of threads as in strain relief 19, substantially the same results can be obtained using friction, circular slots/rings/boss/deboss, knurls, magnets, ball/pin indents, to name a few plausible variations.

The embodiments of the present disclosure can be used in a variety of industrial applications. For example, some embodiments include a method of positioning a medical device using a stabilizing system according to the present disclosure, and such systems, devices, and methods can be used in a medical procedure where manipulation and positioning of a medical device is required and/or desired.

In addition, such systems, devices, and methods can be applied in a medical product testing industry or medical products analysis industry. For example, the ability of a medical device to be supported, positioned, reoriented, and/or manipulated can be tested and analyzed using the devices, systems, and methods of the present disclosure. Further, operational and durability limits of a medical device under such uses can be tested and/or analyzed.

In addition, embodiments of the present disclosure can be used in a medical operator training industry. For example, one or more devices, systems, or methods of the present disclosure can be used in a training application allowing a physician, surgeon, doctor, or medical engineer to undergo training by positioning, manipulating, reorienting, and/or repositioning a medical device.

The terms "approximately", "about," and "substantially" as used herein represent an amount or condition close to the stated amount or condition that still performs a desired function or achieves a desired result. For example, the terms "approximately," "about," and "substantially" may refer to an amount that deviates by less than 10%, or by less than 5%, or by less than 1%, or by less than 0.1%, or by less than 0.01% from a stated amount or condition.

In addition, unless expressly described otherwise, all stated amounts (e.g., angle measurements, dimension measurements, etc.) are to be interpreted as being "approximately," "about," and/or "substantially" the stated amount, regardless of whether the terms "approximately," "about," and/or "substantially" are expressly stated in relation to the stated amount(s).

Further, elements described in relation to any embodiment depicted and/or described herein may be combinable with elements described in relation to any other embodiment depicted and/or described herein.

The present disclosure may be embodied in other specific forms without departing from its spirit or essential characteristics. The described embodiments are to be considered in all respects only as illustrative and not restrictive. The scope of the disclosure is, therefore, indicated by the appended claims and/or clauses rather than by the foregoing description. All changes which come within the meaning and range of equivalency of the claims and/or clauses are to be embraced within their scope.

Although the exemplary embodiments presented here are manual and mechanical, other motorized and/or automated variations that are obvious and/or evident to those skilled in art may be used. For example, direct or indirect or manual or automated or remote controlled by computers, artificial intelligence, motors, magnets, sensors, actuators, and/or transducers may be used to enable controlled manipulation of the catheters, transforming the exemplary pure mechanical and manual stabilizer into "smart" stabilizer. For examples, the stabilizer may have sensors to enable 3D, 2D and/or linear position sensing and actuation that may or may not be transmitted on to a display with or without wires. The display may be local or remote, hand-held or large and not hand-held.

All embodiments described in this invention maybe manufactured using polymers, metals alloys, ceramics, reinforced composites and/or their combinations of organic or inorganic in origin. Further, these components me be optionally covered, wrapped, coated, or the like to improve user experience or procedure outcomes. Suitable coverings can be fabric, web, fibrous, braid, woven or non-woven. The coatings can be metallic, ceramic, polymeric, or combinations thereof. Suitable metallic coatings include titanium, TiN, tantalum, gold, platinum, and alloys thereof. Suitable ceramic and inorganic coatings include titanium dioxide, hydroxyapatite, CaP, and the like. Suitable polymeric coatings include fluoropolymers, e.g. PTFE, PFA, FEP, ECTFE, ETFE; parylene, polyester, PET, polypropylene, PEEK, PVDF, HDPE, LDPE, UHMWPE, phosphorylcholine, THV, and the like. Suitable biodegradable include poly(lactic acid), poly(glycolic acid), polydioxanone, poly(c-caprolactone), polyanhydride, poly(ortho ester), copoly(ether-ester), polyamide, polylactone, poly(propylene fumarate), and their combinations. Such metallic, ceramic and/or polymeric coatings are listed as examples only. Any suitable metal, ceramic, polymer, and combination thereof may be used to produce a desirable coating.

The following is a listing of the reference numbers used in this application:

10 Stabilizer—used to stabilize and/or mount catheters such as the guide and delivery catheters
13 Knob—used to control or stabilize and/or fasten the catheter handle 34. It interacts with exemplary threaded strain relief 19
15 Stabilizer base plate
17 Stabilizing Post—along with the Knob 13 is used to control or stabilize and/or fasten the catheter handle 19
18 Tapped/threaded region of the post 17 that meshes with the threads of the threaded strain relief 19
19 Threaded strain relief of the guide catheter handle 34 and shaft 35 that interacts with the Stabilizer 10, 110, 210, 310, 410
21 Threaded screw of the Knob 13
34 Handle—guide catheter handle
35 Guide catheter shaft
44 Handle—delivery catheter handle
45 Delivery catheter shaft
49 Structural strain relief of the delivery catheter handle 44 and delivery catheter shaft 45
60 Exemplary implant
71 Stabilizing Post—along with the Knob 73 is used to control or stabilize and/or fasten the delivery catheter handle 44
73 Knob—used to control or stabilize and/or fasten the catheter handle 44. It interacts with exemplary strain relief 49
81 Stabilizing Post—along with the Knob 83 is used to control or stabilize and/or fasten the delivery catheter handle 44
83 Knob—used to control or stabilize and/or fasten the catheter handle 44.
93 Gap between the Knob screw and Threaded strain relief 19
95 Gap between the Stabilizing post 17 and Threaded strain relief 19
110 Alternate embodiment of stabilizer with the stabilizing post 117
113 Retractable spring plunger—used to control or stabilize and/or fasten the catheter handle 34. It interacts with exemplary threaded strain relief 19
117 Alternate embodiment of stabilizing post—along with the Knob 13 is used to control or stabilize and/or fasten the catheter handle 19
118 Tapped/threaded region of the post 117 that meshes with the threads of the threaded strain relief 19.
120 Alternate embodiment of stabilizer with the stabilizing post 217
121 Threaded screw of the retractable spring plunger 113.
124 Retractable plunger segment of the retractable spring plunger 113.
210 Alternate embodiment of stabilizer with the stabilizing post 217
217 Alternate embodiment of stabilizing post—along with the Knob 13 is used to control or stabilize and/or fasten the catheter handle 19
218 Tapped/threaded region of the post 217 that meshes with the threads of the threaded strain relief 19.
310 Alternate embodiment of stabilizer with swiveling stabilizing post 317
315 Plates with top holes 325 and bottom hole 328 to mount Swiveling stabilizing post 317
317 Swiveling stabilizer post
325 Top holes of plate 315
327 Quick release pin
328 Bottom hole of plate 315
410 Alternate embodiment of stabilizer with swiveling stabilizing post 317
415 Plates with top slot 425 and bottom hole 328 to mount swiveling stabilizing post 317
425 Top slot on plate 415
435 Screw that fixes the swiveling stabilizing post 317
445 Wing-nut that fixes the swiveling stabilizing post 317
512 Tray mounted on the OR table standard side rail
515 Quick connect clamp to secure exemplary stabilizer 10 to the OR tray 512

522 Interface component between OR tray 512 and articulating arm 526
526 Lockable articulating arm
531 Interface component between articulating arm 526 and/or table standard side rail 537
537 Standard side rail of OR table
560 Slip-on twist-close nut (similar to for example and not limited to this example https://www.mcmaster.com/90125a086)
570 Hex Push-Button Slide-Adjust Nut (similar to for example and not limited to this example https://www.mcmaster.com/98150a150)

General Considerations

Although many embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed methods are described in a particular order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the list of elements means any one or more of the listed elements. For example, the phrase "A, B, and/or C" means "A," "B," "C," "A and B," "A and C," "B and C" or "A, B and C."

What is claimed is:

1. A catheter deployment system comprising:
a first catheter having a catheter body with a distal end and a proximal hub;
gripping features on the catheter body distal of the proximal hub;
a free-standing support structure having at least one support post having a gap for receiving the catheter body; and
a clamp structure on the support structure, the clamp structure comprising a single screw which is configured to be advanced and retracted to cause the clamp structure assume an opened position, a closed position, and a plurality of intermediate positions between the opened and closed positions;
wherein (a) the gripping features of the catheter body may be inserted into and removed from the gap on the clamp structure when the clamp structure is in its opened configuration, (b) the gripping features of the catheter body may be rotated and axially translated within the clamp structure when the clamp structure is in a first intermediate position, (c) the gripping features of the catheter body may be rotated but not axially translated within the clamp structure when the clamp structure is in a second intermediate position, and (d) the gripping features of the body of the first catheter are prevented from both rotation and axial translation within the clamp structure when the clamp structure is its closed position.

2. The catheter deployment system of claim 1, wherein the gripping features comprise circumferential ribs and valleys and the clamp structure has an engaging element located adjacent to the gripping features when the first catheter in the clamp structure.

3. The catheter deployment system of claim 2, wherein the engaging element does not engage the gripping features when the clamp structure is in the first intermediate position such that the first catheter is free to both rotate and axially translate relative to the support structure.

4. The catheter deployment system of claim 2, wherein the engaging element is advanced into the valley between adjacent ribs when the clamp structure is in the second intermediate position such that the catheter is free to rotate as the engaging element travels in the valley but is constrained from axial movement by the ribs.

5. The catheter deployment system of claim 1, further comprising a second catheter configured to be introduced through a lumen of the first catheter while the first catheter is held by the clamp structure.

6. The catheter deployment system of claim 5, wherein the second catheter has a rigid proximal shaft region that self-supports a handle of the second catheter when extending proximally from a proximal end of the first catheter.

7. The catheter deployment system of claim 5, further comprising a second support post on the support structure, wherein the second support post supports a handle of the second catheter when extending proximally from a proximal end of the first catheter.

8. The catheter deployment system of claim 2, wherein the clamp structure comprises a biasing member configured to advance the gripping features toward the engaging element.

9. The catheter deployment system of claim 8, wherein the biasing member comprises a threaded shaft.

10. The catheter deployment system of claim 9, wherein the engaging element comprises a ribbed structure that mates with the ribs of the gripping features.

11. A method for supporting a first catheter during a procedure, said method comprising:
providing a first catheter having a body with a distal end, a proximal hub, and gripping features on the catheter body distal of the proximal hub;
providing a support structure including at least one support post having a gap with a clamp structure comprising a single screw and having an opened position, a closed position, and a plurality of intermediate positions between the opened and closed positions;
advancing and retracting the single screw to reconfigure the clamp in its opened, closed, and intermediate positions;
placing the first catheter into the gap on the support structure so that the gripping features are located in the clamp structure while the clamp structure is in the opened position;
closing the clamp structure to a first intermediate position over the gripping features;
rotating and/or axially translating the catheter about its axis while the clamp structure remains in the first intermediate position;
closing the clamp structure to a second intermediate position over the gripping features;
rotating the first catheter about its axis while the clamp structure remains in the second intermediate position, wherein the clamp structure allows rotation of but prevents axial translation of the first catheter and;
closing the clamp structure to its closed position over the gripping features, wherein the clamp structure allows neither rotation nor axial translation of the first catheter.

12. The method of claim 11, wherein the gripping features comprise circumferential ribs and valleys and wherein closing the clamp structure to the first intermediate position places an engaging element on the clamp structure adjacent to the gripping features without engaging the gripping features.

13. The method of claim 11, wherein closing the clamp structure to the second intermediate position advances the engaging element into the valley between adjacent ribs such that the catheter is free to rotate as the engaging element travels in the valley but is constrained from axial movement by the ribs.

14. The method of claim 11, further comprising introducing a second catheter through a lumen of the first catheter while the first catheter is held on the support structure by the clamp structure.

15. The method of claim 14, further comprising supporting a hub on the second catheter in tandem with the hub on the first catheter.

16. The method of claim 15, wherein supporting the hub on the second catheter in tandem with the hub on the first catheter comprises self-supporting the hub on a rigid proximal shaft region of the second catheter.

17. The method of claim 15, wherein supporting the hub on the second catheter in tandem with the hub on the first catheter comprises placing the hub on a second support post on the support structure.

* * * * *